(12) United States Patent
Whitehurst

(10) Patent No.: US 6,922,590 B1
(45) Date of Patent: Jul. 26, 2005

(54) SYSTEMS AND METHODS FOR TREATMENT OF DIABETES BY ELECTRICAL BRAIN STIMULATION AND/OR DRUG INFUSION

(75) Inventor: Todd K. Whitehurst, Sherman Oaks, CA (US)

(73) Assignee: Advanced Bionics Corporation, Valencia, CA (US)

( * ) Notice: Subject to any disclaimer, the term of this patent is extended or adjusted under 35 U.S.C. 154(b) by 297 days.

(21) Appl. No.: 09/993,085

(22) Filed: Nov. 6, 2001

Related U.S. Application Data

(60) Provisional application No. 60/252,618, filed on Nov. 21, 2000.

(51) Int. Cl.[7] .................................................. A61N 1/18
(52) U.S. Cl. ........................ 607/45; 607/58; 604/891.1
(58) Field of Search ........................... 607/62, 116, 117, 607/118, 61, 60, 44, 45, 72, 73, 3, 2, 66, 500, 58; 604/890.1, 891.1, 66, 500; 600/373, 383, 365

(56) References Cited

U.S. PATENT DOCUMENTS

| | | | |
|---|---|---|---|
| 4,646,744 A | 3/1987 | Capel | |
| 5,188,104 A | 2/1993 | Wernicke et al. | |
| 5,193,539 A | 3/1993 | Schulman et al. | |
| 5,193,540 A | 3/1993 | Schulman et al. | |
| 5,231,988 A | 8/1993 | Wernicke et al. | |
| 5,263,480 A | 11/1993 | Wernicke et al. | |
| 5,312,439 A | 5/1994 | Loeb | |
| 5,324,316 A | 6/1994 | Schulman et al. | |
| 5,405,367 A | 4/1995 | Schulman et al. | |
| 5,487,739 A | 1/1996 | Aebischer et al. | |
| 5,496,369 A | 3/1996 | Howard, III | |
| 5,540,730 A * | 7/1996 | Terry, Jr. et al. | 607/40 |
| 5,540,734 A | 7/1996 | Zabara | |
| 5,597,797 A | 1/1997 | Clark | |
| 5,697,975 A | 12/1997 | Howard, III et al. | |
| 5,589,183 A | 12/1996 | Jannetta | |
| 5,741,211 A | 4/1998 | Renirie et al. | |
| 5,782,798 A | 7/1998 | Rise | |
| 5,843,093 A | 12/1998 | Howard, III | |
| 5,919,216 A | 7/1999 | Houben et al. | |
| 5,989,920 A | 11/1999 | Gerald et al. | |
| 6,006,124 A * | 12/1999 | Fischell et al. | 600/378 |
| 6,016,449 A | 1/2000 | Fischell et al. | |
| 6,051,017 A | 4/2000 | Loeb et al. | |
| 6,093,167 A | 7/2000 | Houben et al. | |
| 6,094,598 A * | 7/2000 | Elsberry et al. | 607/116 |
| 6,129,685 A | 10/2000 | Howard, III | |
| 6,171,239 B1 * | 1/2001 | Humphrey | 600/372 |
| 6,269,270 B1 * | 7/2001 | Boveja | 607/45 |
| 6,284,729 B1 * | 9/2001 | Bernfield et al. | 514/12 |
| 6,353,762 B1 * | 3/2002 | Baudino et al. | 607/45 |
| 6,374,140 B1 * | 4/2002 | Rise | 607/45 |
| 6,415,184 B1 | 7/2002 | Ishikawa et al. | |

FOREIGN PATENT DOCUMENTS

| | | |
|---|---|---|
| WO | WO-92/13592 A1 | 8/1992 |
| WO | WO-93/02743 A1 | 2/1993 |
| WO | WO-98/37926 A1 | 9/1998 |
| WO | WO-98/43700 A1 | 10/1998 |
| WO | WO-98/43701 A1 | 10/1998 |
| WO | WO-01/60450 A1 | 8/2001 |

OTHER PUBLICATIONS

Ahren, et al., "The Mechanism of Vagal Nerve Stimulation of Glucagon and Insulin Secretion in the Dog", Endocrinology, vol. 118, No. 4, (Apr. 1986), pp. 1551–1557.

(Continued)

*Primary Examiner*—Jeffrey R. Jastrzab
(74) *Attorney, Agent, or Firm*—Laura Haburay Bishop

(57) ABSTRACT

Systems and methods for introducing one or more stimulating drugs and/or applying electrical stimulation to the brain to at least treat or prevent diabetes uses at least one system control unit (SCU) producing electrical pulses delivered via electrodes implanted in the brain and/or producing drug infusion pulses, wherein the stimulating drug(s) are delivered to targeted areas in the brain.

24 Claims, 10 Drawing Sheets

OTHER PUBLICATIONS

Ahren, et al., "Sympathetic Nerve Stimulation Versus Pancreatic Norepinephrine Infusion in the Dog: 1. Effects on Basal Release of Insulin and Glucagon", Endocrinology, vol. 121, No. 1, (Jul. 1987), pp. 323–331.

Bereiter, et al., "CNS Modulation of Pancreatic Endocrine Function Multiple Modes of Expression", Diabetologia, Suppl. 20, (Mar. 1981), pp. 417–425.

Berthoud, et al., "Characteristics of Gastric and Pancreatic Responses to Vagal Stimulation with Varied Frequencies: Evidence for Different Fiber Calibers?", Journal of the Autonomic Nervous System, vol. 19, No. 1, (Apr. 1987), pp. 77–84.

Berthoud, et al., "Localization of Vagal Preganglionics that Stimulate Insulin and Glucagon Secretion", AM J Physiol, vol. 258, No. 1 Part 2, (Jan. 1990), pp. R160–R168.

Bluher, et al. "Improvement of Insulin Sensitivity After Adrenalectomy in Patients with Pheochromocytoma", Diabetes Care, vol. 23, No. 10, (Oct. 1, 2000), pp. 1591–1592.

Brobeck, Jr., "Mechanism of Development of Obesity in Animals with Hypothalamic Lesions", Physiol Rev. vol. 26, (1946), pp. 541–559.

Broglio, et al., "Ghrelin, a Natural GH Secretagogue Produced by the Stomach, Induces Hyperglycemia and Reduces Insulin Secretion in Humans", The Journal of Clinical Endocrinology & Metabolism, vol. 86, No. 10, (Oct. 2001), pp. 5083–5086.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781–790.

Davalli, et al., "Abnormal Sensitivity to Glucose of Human Islets Cultured in a High Glucose Medium: Partial Reversibility After an Additional Culture in a Normal Glucose Medium", Journal of Clinical Endocrinology and Metabolism, vol. 72, (1991), pp. 202–208.

DeNicola, et al., "Abnormal Regulation of Adrenal Function in Rats with Streptozotocin Diabetes", Horm Metab Res, vol. 9, (1977), pp. 469–473.

Dhillo, et al., "Hypothalami Peptides as Drug Targets for Obesity", Current Opinion in Pharmacology, vol. 1, No. 6, (2001), pp. 651–655.

Frankish, et al., "Neuropeptide Y, the Hypothalamus, and Diabetes: Insights Into the Central Control of Metabolism", Peptides, vol. 16, No. 4, (1995), pp. 757–771.

Gardemann, et al., "Reinnervation of Pancreatic Islets and Regulation of Insulin Secretion by Hepatic Sympathetic Nerves After Intrportal Transplantation of Islets Into Livers of Diabetic Rats", Experimental and Clinical Endocrinology and Diabetes, vol. 103, Suppl. 2, (1995), pp. 107–111.

Holst, et al., "Nervous Control of Pancreatic Endocrine Secretion in Pigs. I. Insulin and Glucagon Responses to Electrical Stimulation of the Vagus Nerves", Acta Physiol Scand, vol. 111, No. 1, (Jan. 1981), pp. 1–7.

Hyde, et al., "Effects of Area Postrema Caudal Medial Nucleus of Solitary Tract Lesions on Food Intake and Body Weight", AM J Physiol, vol. 244, (1983), pp. R577–R587.

Ionescu, et al., "Increase in Plasma Insulin Levels in Response to Electrical Stimulation of the Dorsal Motor Nucleus of the Vagus Nerve", Endocrinology, vol. 112, No. 3, (Mar. 1983), pp. 904–910.

Jonkers, et al., "Influence of Cell Number on the Characteristics and Synchrony of Ca2+ Oscillations in Clusters on Mouse Pancreatic Islet Cells", Journal of Physiology, vol. 520, Part 3, (Nov. 1999), pp. 839–849.

Kakizaki, et al., "Neural Regulation of Auto–Grafted Islets of Langerhans", Nippon Geka Gakkai Zasshi, vol. 89, No. 3, (Mar. 1988), pp. 394–397.

Kakizaki, et al., "Neural Regulation of Heterotopic Islets of Langerhans", Surgery, vol. 100, No. 6, (Dec. 1986), pp. 997–1002.

Kurose, et al., "Glucagon, Insulin and Somatostatin Secretion in Response to Sympathetic Neural Activation in Streptozotocin0induced Diabetic Rats. A Study with the Isolated Perfused Rat Pancreas in Vitro", Diabetologia, vol. 35, No. 11, (Nov. 1992), pp. 1035–1041.

Kurose, et al., "Mechanism of Sympathetic Neural Regulation of Insulin, Somatostatin, and Glucagon Secretion", Am J Physiol, vol. 258, No. 1 part 1, (Jan. 1990), pp. E220–E227.

Lorrain, et al., "Adrenergic and Nonadrenergic Cotransmitters Inhibit Insulin, Secretion During Sympathetic Stimulation in Dogs", AM J Physiol, vol. 263, No. 1 Part 1, (Jul. 1992), pp. E72–E78.

Mayfield, et al., "A Role for the Agouti–Related Protein Promoter in Obesity and Type 2 Diabetes", Biochemical and Biophysical Research Communications, vol. 287, No. 2, (Sep. 21, 2001), pp. 568–573.

Minami, et al., "Electrophysiological Properties and Glucose Responsiveness of Guinea–Pig Ventromedial Hypothalamic Neurons in Vitro", J. Physiol, vol. 380, (1986), pp. 127–143.

Misler, et al., "Electrophysiology of Stimulus–Secretion Coupling in Human Beta–Cells", Diabetes, vol. 41, No. 10, (Oct. 1992), pp. 1221–1228.

Mondal, et al., "Orexins (hypocretins): Novel Hypothalami Peptides with Divergent Functions", Biochem Cell Biol, vol. 78, (2000), pp. 299–305.

Nakazato, et al., "A Role for Ghrelin in the Central Regulation of Feeding", Nature, vol. 409, No. 6817, (Jan. 11, 2001), pp. 194–198.

Nishi, et al., "Vagal Regulation of Insulin, Glucagon, and Somatostatin Secretion in Vitro in the Rat", J Clin Invest, vol. 79, No. 4, (Apr. 1987), pp. 1191–1196.

Oomura, et al., "Glucose and Osmosensitive Neurons of the Rat Hypothalamus", Nature, vol. 222, (1969), pp. 282–284.

Perkins, et al., "Activation of Brown Adipose Tissue Thermogenesis by the Ventromedial Hypothalamus", Nature, vol. 289, (Jan. 1981), pp. 401–402.

Pierroz, et al., "Chronic Administration of Neuropeptide Y into the Lateral Ventricle Inhibits Both the Pituitary–Testicular Axis and Growth Hormone and Insulin–Like Growth Factor I Secretion in Intact Adult Male Rats", Endocrinology, vol. 137 No. 1, (Jan. 1996), pp. 3–12.

Pi–Sunyer, "Pathogenesis of Obesity", Drug Benefit Trends, vol. 12, Supp A, (2002), pp. 28–33.

Qu, et al., "Agouti–Related Protein is a Mediator of Diabetic Hyperphagia", Regulatory Peptides, vol. 98, No. 1–2, (Apr. 2, 2001), pp. 69–75.

Ratner, "Innovations in Managing Type 2 Diabetes", Drug Benefit Trends, vol. 12, Supp A, (2000), pp. 34–43.

Ravier, et al., "Oscillations of Insulin Secretion Can be Triggered by Imposed Oscillations of Cytoplasmic Ca2+ or Metabolism in Normal Mouse Islets", Diabetes, vol. 48, No. 12, (Dec. 1999), pp. 2374–2382.

Sahu, et al., "Evidence that Neurotensin Mediates the Central Effect of Leptin on Food Intake in Rat", Brain Research, vol. 888, No. 2, (Jan. 12, 2001), pp. 343–347.

Sawchenko, et al., "The Distribution of Cells of Organ of Serotonin Input to the Paraventricular and Supraoptic Nuclei of the Rat", Brain Research, vol. 277, (1983) pp. 355–360.

Shor–Posner, et al., "Deficits in the Control of Food Intake After Paraventricular Nucleus Lesions", Physiology and Behavior, vol. 35, (1985), pp. 883–890.

Tanaka, et al., "Effects of Intraventricular Administration of Neuropeptide Y on Feeding Behavior in Fasted Female Rats with Ventromedial Hypothalamic Lesions", Regulatory Peptides, vol. 52, No. 1, (Jun. 16, 1994) pp. 47–52.

Thomas, eta l., "Reversal of Type II (NIDDM) Diabetes by Pancreas Islet Transplantation: an Emerging New Concept in Pathophysiology of an Enigmatic Disease", Transplantation Proceedings, vol. 27, No. 6, (Dec. 1995), pp. 3167–3169.

Zaborszky, et al., "Brainstem Projection to the Hypothalamic Paraventricular Nucleus in the Rat, a CCK–Containing Long Ascending Pathway", Brain Research, vol. 303, (1984), pp. 225–231.

"Hormones Found in the Brain May Determine How Much You Eat and Affect Obesity and Diabetes", printed Dec. 12, 2002, pp. 1–2.

"Neurogen Commences Phase Ib Human Clinical Trials with Anti–Obesity Drug", printed Dec. 6, 2002, p. 1.

"Obesity: Mechanism: Neuropeptide Y Receptor Antagonists", Neurogen Corporation, printed Aug. 21, 2002, pp. 1–2.

Wahlestedt, et al. "Neuropeptide Y and Related Peptides", printed Jul. 10, 2001, pp. 1–10.

Wells, William A., "Possible Finding on Weight Control", Standford online Report, printed Dec. 9, 2002, pp. 1–3.

Clore Laboratory: News Diabetes, Obesity and Metabolic Research, "Jun. 7, 2001—Hot topic poster European Obesity Congress", printed Dec. 12, 2002, p. 1.

Whitehurst inventor for AB–135U; U.S. Appl. No. 09/993, 086; filed Nov. 6, 2001; entitled "Systems and Methods for Treatment of Obesity and Eating Disorders by Electrical Brain Stimulation and/or Drug Infusion".

Whitehurst and McGivern inventors for AB–147U; U.S. Appl. No. 09/993,084; filed Nov. 6, 2001; entitled "Systems and Methods for Modulation of Pancreatic Endocrine Secretion and Treatment of Diabetes".

\* cited by examiner

SYSTEMS AND METHODS FOR TREATMENT OF DIABETES BY ELECTRICAL BRAIN STIMULATION AND/OR DRUG INFUSION

The present application claims the benefit of U.S. Provisional Patent Application Ser. No. 60/252,618, filed Nov. 21, 2000, which application is incorporated herein by reference in its entirety.

FIELD OF THE INVENTION

The present invention generally relates to drug delivery and electrical simulation systems and methods, and more particularly relates to utilizing one or more devices to deliver electrical stimulation and/or one or more stimulating drugs to certain areas of the brain as a treatment for diabetes.

BACKGROUND OF THE INVENTION

Twelve to fifteen million people in the United States suffer from diabetes mellitus (which is often, as herein, simply referred to as diabetes). Diabetes is a syndrome characterized by disordered metabolism and inappropriately high levels of blood glucose, i.e., hyperglycemia. Diabetes is classified into two distinct types. Type 1, also known as Insulin-Dependent Diabetes Mellitus (IDDM), is believed to be due to autoimmune destruction of beta cells in the pancreas, which are the only cells in the body that produce and secrete insulin. Type 1 occurs most commonly in juveniles but occasionally in adults. Type 2, also known as Non-Insulin-Dependent Diabetes Mellitus (NIDDM), is a milder form of diabetes that usually occurs in adults.

People with NIDDM have pancreatic beta cells that produce at least a small amount of insulin and that may produce a normal or even excessive amount of insulin. However, organs and tissues in their body do not respond normally to insulin and instead demonstrate a blunted response; this decreased response to insulin is commonly referred to as "insulin resistance." At least 90% of people with diabetes have type 2 diabetes, but an estimated 50% of these people remain undiagnosed.

Current therapies for diabetes tend to focus on restoring insulin and/or on enhancing its effects. Additional treatment options are needed.

SUMMARY OF THE INVENTION

The invention disclosed and claimed herein provides systems and methods for introducing one or more stimulating drugs and/or applying electrical stimulation to one or more areas of the brain for treating or preventing diabetes. Stimulation of specific sites in the brain via Deep Brain Stimulation (DBS) may lead to changes in insulin production, changes in response to insulin, and/or changes in levels or responses to neurotransmitters, hormones, and/or other substances in the body.

The invention is carried out via one or more system control units (SCUs) that apply electrical stimulation and/or one or more stimulating drugs to one or more predetermined stimulation sites in the brain. In some forms of an SCU, one or more electrodes are surgically implanted to provide electrical stimulation from an implantable signal/pulse generator (IPG) and/or one or more infusion outlets and/or catheters are surgically implanted to infuse drug(s) from an implantable pump. In other forms of an SCU, a miniature implantable neurostimulator (a.k.a., a microstimulator), such as a Bionic Neuron (also referred to as a BION® microstimulator), is implanted. Some forms of the disclosed systems also include one or more sensors for sensing symptoms or conditions that may indicate a needed treatment.

An SCU may provide both electrical stimulation and one or more stimulating drugs when necessary and/or desired. In some embodiments, the SCU is implanted in a surgically-created shallow depression or opening in the skull, such as in the temporal bone, padetal bone, or frontal bone. In some such embodiments, one or more electrode leads and/or catheters attached to the SCU run subcutaneously to an opening in the skull and pass through the opening into or onto the brain parenchyma and surrounding tissue.

Patients with diabetes will likely respond to therapeutic excitatory stimulation applied to those areas of the brain that exhibit chronic decreased activity relative to normal control subjects. Thus, according to certain embodiments of the invention, the stimulation increases excitement of one or more of those areas of the brain that exhibit chronic decreased activity in diabetic patients relative to normal control subjects, thereby treating or preventing diabetes and/or the symptoms and/or consequences thereof. Such excitatory stimulation is likely to be produced by, for example, low-frequency electrical stimulation, an excitatory neurotransmitter agonist, and/or an excitatory hormone agonist. Additional potential (but not necessary) uses of the present invention include, but are not limited to, application to diabetes prevention (e.g., via the promotion of normal metabolism and weight reduction), obesity and other eating disorders, and other metabolic disorders.

Patients with diabetes will likely respond to therapeutic inhibitory stimulation applied to those areas of the brain that exhibit chronic increased activity relative to normal control subjects. Thus, according to various embodiments of the invention, the stimulation decreases excitement of one or more of those areas of the brain that exhibit chronic increased activity in diabetic patients relative to normal control subjects, thereby treating or preventing diabetes and/or the symptoms and/or consequences thereof. Such inhibitory stimulation is likely to be produced by, for example, high-frequency electrical stimulation, an inhibitory neurotransmitter agonist, and/or an inhibitory hormone agonist. Again, additional potential (but not necessary) uses include, but are not limited to, application to diabetes prevention, to obesity, and to other eating disorders.

The SCU may include a programmable memory for storing data and/or control parameters. This allows stimulation and control parameters to be adjusted to levels that are safe and efficacious with minimal discomfort. Electrical and drug stimulation may be controlled independently; alternatively, electrical and drug stimulation may be coupled, e.g., electrical stimulation may be programmed to occur only during drug infusion.

According to some embodiments of the invention, the electrodes used for electrical stimulation are arranged as an array on a thin implantable lead. The SCU may be programmed to produce either monopolar electrical stimulation, e.g., using the SCU case as an indifferent electrode, or bipolar electrical stimulation, e.g., using one of the electrodes of the electrode array as an indifferent electrode. The SCU may include a means of stimulating a nerve or infusing a stimulating drug(s) either intermittently or continuously. Specific stimulation/infusion parameters may provide therapy for, e.g., varying types and degrees of severity of diabetes.

The SCU used with the present invention possesses one or more of the following properties, among other properties:

at least two electrodes for applying stimulating current to surrounding tissue and/or a pump and at least one outlet for delivering a drug or drugs to surrounding tissue;

electronic and/or mechanical components encapsulated in a hermetic package made from biocompatible material(s);

an electrical coil inside the package that receives power and/or data by inductive or radio-frequency (RF) coupling to a transmitting coil placed outside the body, avoiding the need for electrical leads to connect devices to a central implanted or external controller;

means for receiving and/or transmitting signals via telemetry;

means for receiving and/or storing electrical power within the SCU; and a form factor making the SCU implantable in a depression or opening in the skull, or within the brain.

The power source of the SCU is realized using one or more of the following options, or the like:

(1) an external power source coupled to the SCU via a radio-frequency (RF) link;

(2) a self-contained power source made using any means of generation or storage of energy, e.g., a primary battery, a replenishable or rechargeable battery, a capacitor, a supercapacitor; and/or (3) if the self-contained power source is replenishable or rechargeable, a means of replenishing or recharging the power source, e.g., an RF link, an optical link, or other energy-coupling link.

According to certain embodiments of the invention, an SCU operates independently. According to various embodiments of the invention, an SCU operates in a coordinated manner with other implanted SCUs, other implanted devices, or with devices external to the patient's body.

According to several embodiments of the invention, an SCU incorporates means of sensing the disorder or symptoms thereof, or other measures of the state of the patient. Sensed information may be used to control the electrical and/or drug stimulation parameters of the SCU in a closed loop manner. According to some embodiments of the invention, the sensing and stimulating means are incorporated into a single SCU. According to several embodiments of the invention, the sensing means communicates sensed information to at least one SCU with stimulating means.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1A:
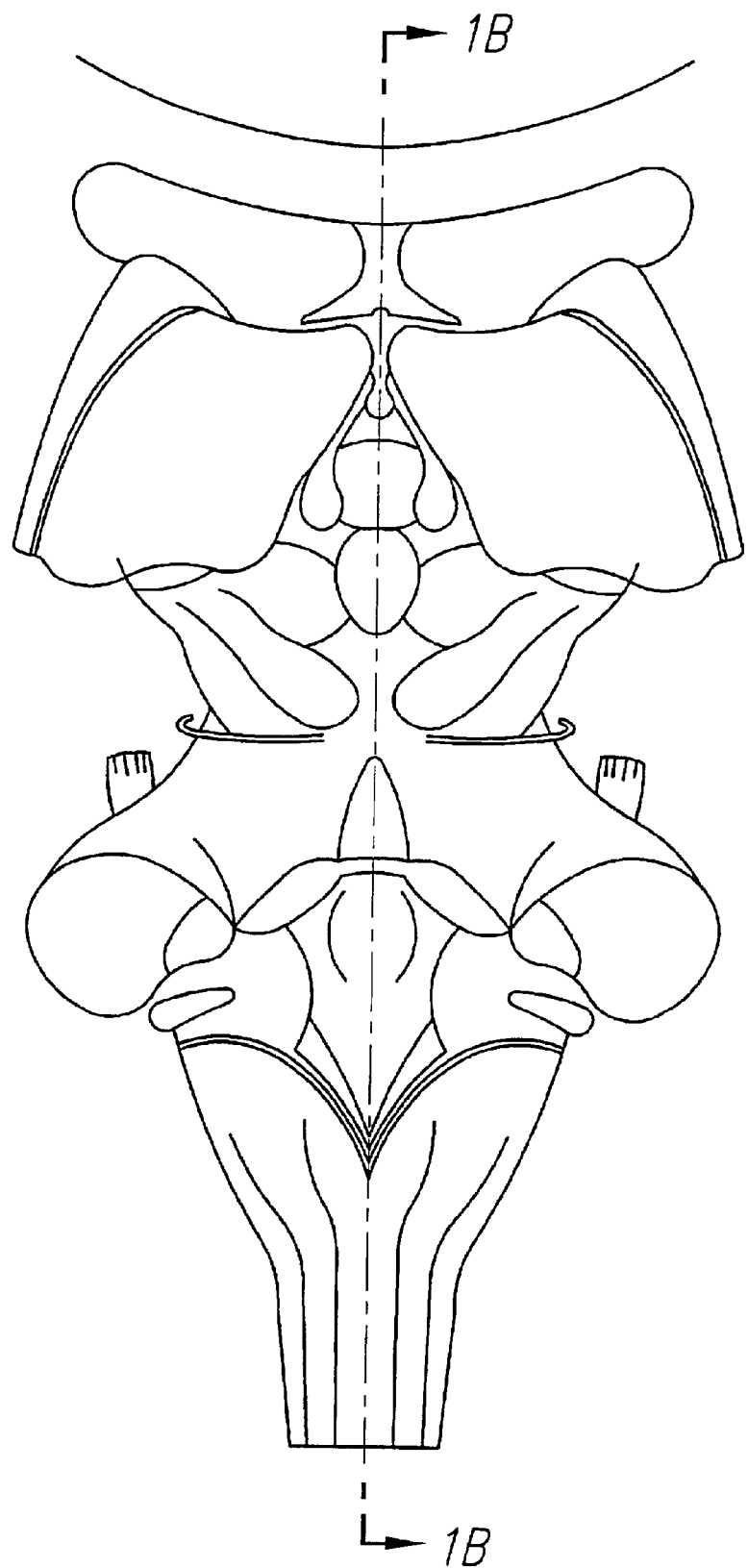
FIG. 1A depicts the dorsal surface of the brain stem.

The following description is of the best mode presently contemplated for carrying out the invention. This description is not to be taken in a limiting sense, but is made merely for the purpose of describing the general principles of the invention. The scope of the invention should be determined with reference to the claims.

The hyperglycemia that is characteristic of diabetes is due either to an absolute deficiency of insulin secretion or a reduction in its biological effectiveness or both. Part of the increased blood glucose level is due to a decreased uptake of glucose by muscle and adipose (i.e., fat) tissue following an intake of food. This uptake is normally stimulated by insulin, but type 2 diabetics display insulin resistance, wherein their muscle and adipose cells uptake a relatively decreased amount of glucose in response to a given level of insulin.

Type 2 diabetics also demonstrate an abnormal liver response to insulin. The liver (along with skeletal muscle) is the body's storage site for glucose. When blood glucose is high, the liver uptakes glucose and converts it to a storage form (i.e., glycogen). Conversely, when blood glucose is low, the liver releases glucose from its storage form. When blood glucose remains low (e.g., during fasting), the liver also produces glucose from amino acids, lipids, and simple carbohydrates via a process known as gluconeogenesis.

Insulin normally inhibits gluconeogenesis, and it normally promotes uptake and conversion of glucose to its storage form in the liver. In persons with type 2 diabetes, gluconeogenesis continues despite the presence of insulin. This lack of liver response to insulin is a characteristic of insulin resistance, and the resulting excessive gluconeogenesis contributes to hyperglycemia.

The insulin resistance of type 2 diabetes (and possibly the non-physiologic insulin levels of type 1 diabetics) may lead to other metabolic disorders in addition to hyperglycemia. Adipose tissue and the liver act to maintain normal blood levels of low-density lipoprotein (LDL) cholesterol, high density lipoprotein (HDL) cholesterol, and triglycerides. A normal insulin response is required for normal regulation of these tissues. Additionally, the diabetic state permits fat to be used as an alternative fuel via ketogenesis. During ketogenesis, fats and proteins travel to the liver, which uses them to produce ketone bodies, which are used as fuel by other tissues. Ketogenesis leads to increased blood levels of LDL cholesterol, decreased HDL cholesterol, and increased triglycerides in diabetics.

During the usually slow transition from normal glucose tolerance to type 2 diabetes, patients suffer from insulin resistance, poorly regulated hepatic (i.e., liver) glucose production, impaired glucose tolerance, and declining beta cell function. In the early stages of the disease, insulin levels tend to be elevated as pancreatic beta cells produce increasing amounts of insulin to overcome insulin resistance. However, as the disease progresses, beta cells become "exhausted" and are no longer able to produce excessive levels of insulin. Insulin levels may then begin to return to "normal" levels and may even fall to relatively low levels. This lack of insulin results in sustained hyperglycemia, which may further damage beta cells due to the phenomenon termed glucotoxicity. Experiments have demonstrated that glucotoxicity and beta cell exhaustion are separate phenomena.

Diabetes, a chronic illness, may lead to a number of complications that may be detrimental to quality of life and that may even significantly reduce life-span. These complications include obesity, atherosclerosis, and hypertension, which may further result in cardiovascular, cerebrovascular, and peripheral vascular diseases. Additional complications of diabetes include retinopathy (which may lead to blindness), nephropathy (which may lead to kidney failure and dialysis), and neuropathy (which may lead to muscular atrophy and/or a host of other conditions).

Obesity is one of the primary risk factors for the development of type 2 diabetes. In fact, some patients are able to decrease the seventy of type 2 diabetes through weight reduction.

As mentioned earlier, current therapies for diabetes tend to focus on restoring insulin and/or on enhancing its effects. Diabetics that are dependent on insulin face daily skin pricks to monitor glucose levels and daily intravenous injections to administer insulin. (insulin, a small protein, is significantly degraded if taken orally and therefore must be administered parenterally.) A small number of diabetics use an external or implanted pump for insulin administration, but they must still monitor their glucose level daily via skin pricks and must periodically refill and maintain their pumps. Inhaled forms of insulin and long-term glucose sensors are under development but are not currently available.

While patients with type 2 diabetes may become insulin-dependent as the disease progresses, the majority may be treated with dietary modifications, lifestyle modifications, and oral medications. Obesity is a common comorbid condition of type 2 diabetes, and an increase in physical exercise and a decrease in body mass may effect some reversal of type 2 diabetes. However, patients rarely achieve such a reversal.

Oral medications for the treatment of type 2 diabetes include agents that promote greater insulin release (e.g., meglitinides, such as repaglinide, and also sulfonylureas), agents that increase cell response to insulin (e.g., thiazolidinediones, such as troglitazone, rosiglitazone, and pioglitazone, and also biguanides), agents that delay the digestion and absorption of carbohydrates (i.e., alphaglucosidase inhibitors, such as acarbose and miglitol), and agents that suppress hepatic gluconeogenesis (e.g., the biguanide called metformin). However, in most patients, diabetes and its associated complications progress despite dietary modifications and oral medications, albeit at a slower rate.

The secretion of insulin by the pancreatic beta cells is neurally modulated via autonomic input from the brain. Parasympathetic input via branches of the vagus nerve tends to increase secretion of insulin. In contrast, sympathetic input via branches of the splanchnic nerve (from the paraspinal sympathetic ganglia) tends to decrease secretion of insulin.

Mechanisms in the brain that may contribute to complications of diabetes have only recently begun to be elucidated. The hypothalamus is now understood to be the primary control center of the body in determining food intake, energy expenditure, and fat content. The hypothalamus is divided into small functional collections of cells known as nuclei; one or more nuclei in the hypothalamus may demonstrate abnormal behavior in diabetics.

The arcuate nucleus of the hypothalamus is one of the primary sites of such dysfunction. The arcuate nucleus lies functionally outside the blood-brain barrier and contains abundant receptors for insulin, leptin, and glucocorticoids. Some of the neurons in the arcuate nucleus secrete a neurotransmitter known as Neuropeptde Y (NPY). These NPY-secreting neurons project to several other hypothalamic nuclei. Increased secretion of NPY leads to increased feeding (hyperphagia), increased body weight, and reduced energy expenditure. In fact, NPY is the most potent central (i.e., acts in the brain/spinal cord) appetite stimulant known. In addition, it is believed that unfavorable metabolic situations, such as diabetes, produce enhanced NPY gene expression and NPY release in the hypothalamus.

NPY also leads to endocrinological disturbances, including increased secretion of adrenocorticotrophic hormone (ACTH) and glucocorticoids, and decreased secretion of luteinizing hormone (LH), follicle-stimulating hormone (FSH), growth hormone (GH), and thyroid stimulating hormone (TSH). Increased levels of glucocorticoids stimulate feeding, favor fat accumulation, and are essential to the development of obesity in rats. ACTH and glucocorticoid levels have been found to be increased in diabetics.

Insulin is believed to inhibit the release of NPY, and NPY levels are elevated in patients with type 2 diabetes. Leptin, a protein secreted by adipose cells, is believed to inhibit NPY neurons in the arcuate nucleus. In normal subjects, leptin acts via the leptin receptor in the hypothalamus to cause hypophagia, increased heat generation (thermogenesis), and loss of body fat. However, mice with an absence of leptin or with a defect in the hypothalamic leptin receptor develop obesity and severe insulin resistance. Serotonin is also believed to inhibit the secretion of NPY.

The paraventricular nucleus of the hypothalamus receives significant input from the NPY-secreting neurons of the arcuate nucleus. Neuronal pathways descend from the paraventricular nucleus to the dorsal motor nucleus of the vagus nerve in the brainstem, and neurons from there ultimately provide parasympathetic input to the pancreatic beta cells, thus increasing insulin secretion in normal subjects. Destruction of the region of the paraventricular nucleus leads to hyperphagia, reduced energy expenditure, and obesity. Excess NPY may also promote these effects. Hypoglycemia and other stressors stimulate the release of corticotrophin-releasing factor (CRF) from the CRF secreting neurons of the paraventricular nucleus, which ultimately leads to increase levels of ACTH and glucocorticolds.

The dorsomedial nucleus of the hypothalamus also receives significant input from the NPY-secreting neurons of the arcuate nucleus. It integrates additional information from the adjacent ventromedial nucleus and the lateral hypothalamic area. Again, increased levels of NPY lead to hyperphagia, increased body weight, and reduced energy expenditure.

The ventromedial nucleus contains glucoceptor neurons that respond to low levels of blood glucose, and electrical stimulation of the ventromedial nucleus triggers an increase in blood glucose. Neuronal pathways descend from the ventromedial nucleus to ultimately provide sympathetic input to the pancreatic beta cells, thus decreasing insulin secretion in normal subjects. The ventromedial nucleus also triggers sympathetic activity to raise blood glucose levels and stimulate heat production and energy expenditure. Destruction of the region of the ventromedial nucleus leads to hyperphagia, reduced energy expenditure, obesity, and, through parasympathetic activation, increased blood levels of insulin in otherwise normal subjects. In addition, for centrally administered NPY, the ventromedial nucleus is believed to be a crucial site of NPY-induced feeding.

The lateral hypothalamic area also contains glucose-sensitive neurons which also respond to insulin. However, the lateral hypothalamic area acts to inhibit thermogenesis and gluconeogenesis, thus lowering blood glucose levels. Destruction of the region of the lateral hypothalamic area leads to anorexia and wasting. Increased activation of the lateral hypothalamus (via electrical stimulation) in anesthetized rats produces both an inhibitory component of insulin secretion, probably related to sympathetic stimulation, and a stimulatory component, probably due to the release into the blood of factor(s) that promote insulin secretion.

The nucleus of the solitary tract lies in the brainstem, but it projects to the hypothalamus. It receives gustatory (i.e., sense of taste) and other signals (e.g., glucose availability in the liver) via afferent nerve fibers, as well as through direct contact with systemic circulation (via fenestrated capillaries that allow circulating proteins and other substances to bypass the blood-brain barrier). The nucleus of the solitary tract is involved in controlling energy homeostasis, and destruction in the region of this nucleus leads to increased consumption of food. Stimulation of the nucleus of the solitary tract, which is anatomically connected to the dorsal motor nucleus of the vagus nerve in the brainstem, produces a 50% increase in blood levels of insulin in normal subjects.

The dorsal motor nucleus of the vagus nerve is the primary source of efferent parasympathetic nerve fibers that travel via the vagus nerve to the pancreas and ultimately stimulate increased insulin secretion. Increased activation of the dorsal motor nucleus of the vagus nerve (via electrical stimulation at 30 Hz) was demonstrated in normal anesthetized rats to result in a rapid (within 1 minute) rise in blood levels of insulin (greater than or equal to 200%). Specifically, the parasympathetic neurons that occupy the medial two-thirds of the right and left dorsal motor nucleus are likely to play the predominant role in parasympathetic control of the endocrine pancreas via the vagus nerve.

Ghrelin, a peptide hormone, has been shown to increase food intake in rats under conditions of both fasting and satiety. Furthermore, ghrelin antagonists have been demonstrated to suppress feeding in rats. Ghrelin acts on the arcuate nucleus in the hypothalamus, among other sites, and appears to act as a leptin antagonist.

In eleven normal young volunteers, administration of ghrelin induced a very marked increase in growth hormone (GH) secretion, which was not modified by placebo. Placebo administration also did not modify insulin and glucose levels. However, ghrelin administration induced a prompt increase in serum glucose level and a decrease in serum insulin level. These researchers concluded that, besides stimulating GH secretion, ghrelin is a hormone possessing metabolic actions such as a hyperglycemic effect and a lowering effect on insulin secretion in humans, at least after acute administration. This research also suggests that ghrelin antagonists may be useful in increasing serum insulin levels and in decreasing serum glucose levels.

Agouti-Related Protein (AGRP) is present in increased levels in obese and diabetic mice. It is produced in the hypothalamic arcuate nucleus and can stimulate hyperphagia when over expressed. The type of AGRP produced may vary slightly between individual humans; the variation may be as minor as a difference in one amino acid in the protein. One of these types has been demonstrated to be significantly associated with high body mass index (BMI, a measure of obesity) and type 2 diabetes in Africans. Medications that either block the production or action of AGRP may be effective in treating diabetes, especially type 2 diabetes. AGRP switches off the melanocortin 4 receptor (MC4-R) and possibly the melanocortin 3 receptor (MC3R), among others. Thus, medications that stimulate the MC4-R and/or the MC3-R may also be effective in treating diabetes, especially type 2 diabetes.

Rats rendered diabetic by streptozotocin displayed marked hyperglycemia and hyperphagia and also displayed a nearly 300% increase in hypothalamic AGRP messenger RNA (along with a nearly 200% increase in hypothalamic NPY messenger RNA). Insulin treatment of diabetic rats partially corrected blood glucose and ameliorated hyperphagia. Insulin replacement was also associated with a return to near baseline of hypothalamic AGRP messenger RNA and NPY messenger RNA from the elevated levels that were observed in untreated diabetic rats. These data indicate that AGRP is a mediator of diabetic hyperhpagia and suggest that insulin can directly influence hypothalamic AGRP and NPY messenger RNA expression. They also indicate that measurement of levels of AGRP and NPY in the hypothalamus may be used as an indicator of hyperglycemia.

Orexin-A and orexin-B are neuropeptides found in the lateral hypothalamus. These neuropeptides and their associated receptors, OX1R and OX2R, have been demonstrated to stimulate the appetite of laboratory rats. Both increase food intake in a dose-related fashion, with orexin A significantly more effective than orexin B. Furthermore, when the food intake of the rats was limited, even more of the neuropeptides was produced, as might be expected of a hormone that physiologically regulates appetite. In a recent study, Andrea Haynes of the Clore Laboratory, University of Buckingham demonstrated that a recently developed orexin-1 receptor antagonist, SB 334867A, ameliorated both obesity and diabetes in an animal model of obesity and type 2 diabetes. This antagonist reduced food intake by 10% but increased metabolic rate by 40%, thereby producing a favorable change in metabolic balance. Blood glucose concentrations in the fed state were restored to the normal range by SB 334867A. An OX1 R antagonist such as SB 334867A may be more effective and may have fewer side effects when administered near its target site in the hypothalamus.

The hypothalamic areas that regulate metabolism receive input from many other structures in the brainstem, cerebral cortex, and structures of the limbic system of the brain. Additional substances that may act on the hypothalamus to contribute to the development of diabetes or the symptoms thereof include catecholamines, such as epinephrine and norepinephrine. Various adrenergic and noradrenergic cell groups in the medulla project to the paraventricular nucleus and the dorsomedial nucleus of the hypothalamus. It has been shown that high catecholamine (e.g. norepinephrine and epinephrine) plasma concentrations can exacerbate and even cause diabetes by increasing insulin resistance and/or decreasing insulin secretion.

Additional substances that may act on the hypothalamus to retard or prevent the development of diabetes or the symptoms thereof include corticotropin releasing factor (CRF), bombesin, glucagon-like peptide 1, serotonin, and cholecystokinin. For instance, the arcuate nucleus and the paraventricular nucleus receive serotonergic input from fibers in the raphe nuclei in the brainstem. Serotonin is believed to block the secretion of NPY. The ventromedial nucleus and the paraventricular nucleus of the hypothalamus also receive a cholecystokinin-containing projection relayed from the vagal nuclei via the parabrachial nucleus in the pons (i.e., the pontine taste center).

Low-frequency electrical stimulation (i.e., less than about 100–150 Hz) has been demonstrated to excite neural tissue, leading to increased neural activity. Similarly, excitatory neurotransmitters, agonists thereof, and agents that act to increase levels of an excitatory neurotransmitter(s) have been shown to excite neural tissue, leading to increased neural activity. Inhibitory neurotransmitters have been shown to inhibit neural tissue, leading to decreased neural activity; however, antagonists of inhibitory neurotransmitters and agents that act to decrease levels of an inhibitory neurotransmitter(s) tend to excite neural tissue, leading to increased neural activity.

High-frequency electrical stimulation (i.e., greater than about 100–150 Hz) is believed to have an inhibitory effect on neural tissue, leading to decreased neural activity. Similarly, inhibitory neurotransmitters, agonists thereof, and agents that act to increase levels of an inhibitory neurotransmitter(s) have an inhibitory effect on neural tissue, leading to decreased neural activity. Excitatory neurotransmitters have been demonstrated to excite neural tissue, leading to increased neural activity; however, antagonists of excitatory neurotransmitters and agents that act to decrease levels of an excitatory neurotransmitter(s) inhibit neural tissue, leading to decreased neural activity.

Electrical stimulation has been proposed for treating diabetes. However, electrical stimulation was applied either to the pancreas (U.S. Pat. Nos. 5,919,216 and 6,093,167) or to the vagus nerve (U.S. Pat. No. 5,231,988). In addition, these devices require significant surgical procedures for placement of electrodes, catheters, leads, and/or processing units. These devices may also require an external apparatus that needs to be strapped or otherwise affixed to the skin.

Deep Brain Stimulation (DBS) has been applied to the treatment of central pain syndromes and movement disorders, and it is currently being explored as a therapy for epilepsy. For instance, U.S. Pat. No. 6,016,449 to Fischell, et al. discloses a system for the electrical stimulation of areas in the brain for the treatment of certain neurological diseases such as epilepsy, migraine headaches and Parkinson's disease. However, Fischell et al. do not teach or suggest the use of such a system for the treatment of diabetes.

Figure 1B:
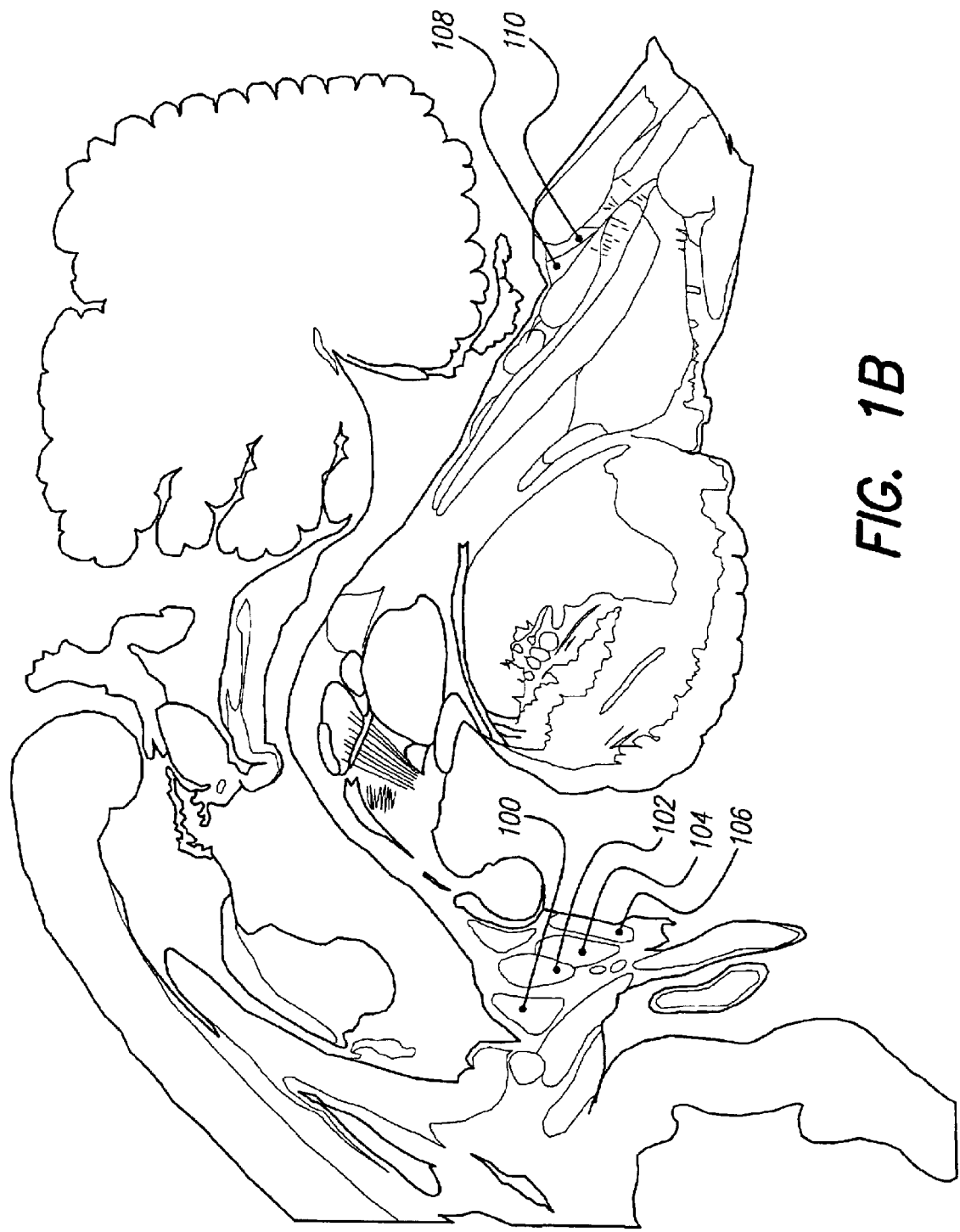
FIG. 1B is a section view through the brain stem depicted in FIG. 1A.
Figure 2A:
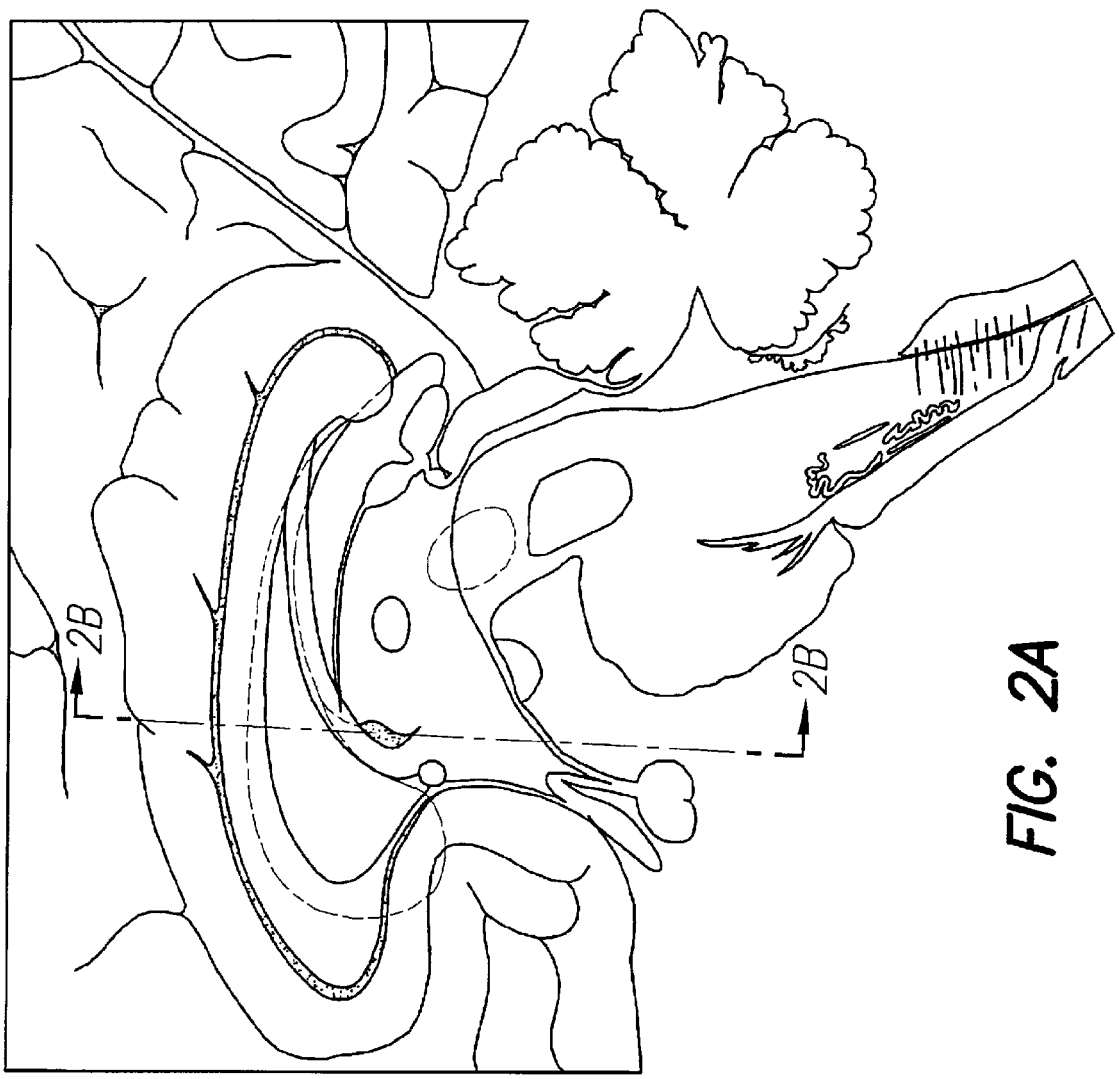
FIG. 2A depicts the medial surface of the brain stem.
Figure 2B:
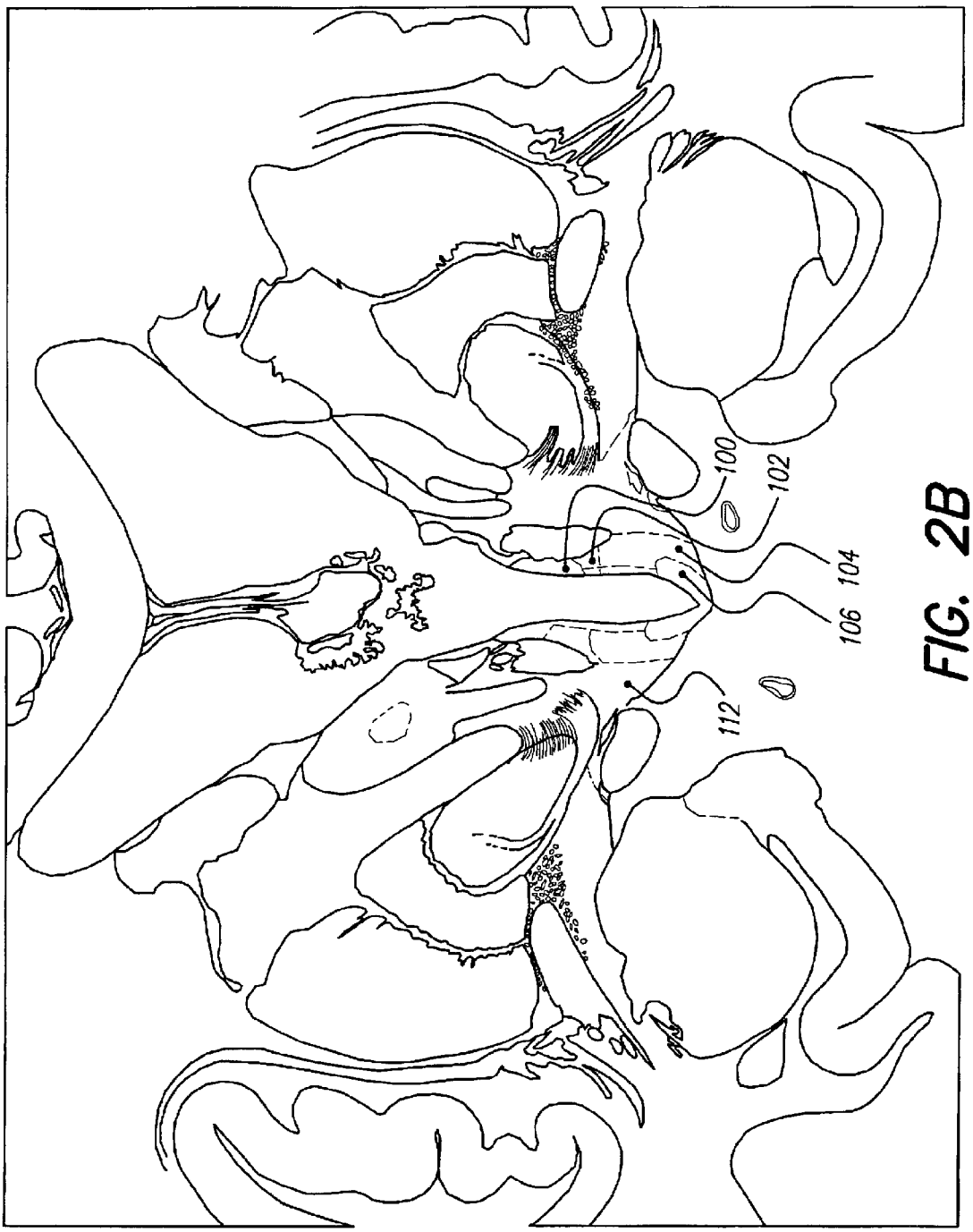
FIG. 2B is a section view through the brain stem depicted in FIG. 2A.

As described above, several hypothalamic nuclei, and other neural tissue within the brain, demonstrate abnormal behavior in diabetics. FIG. 1A depicts the dorsal surface of the brain stem, and FIG. 1B is a section view through the brain stem depicted in FIG. 1A, showing the locations of some of these hypothalamic nuclei: paraventricular nucleus 100, dorsomedial nucleus 102, ventromedial nucleus 104, and arcuate nucleus 106. FIG. 1B also shows the dorsal motor nucleus of the vagus nerve 108 and the nucleus of the solitary tract 110. FIG. 2A depicts the medial surface of the brain stem, and FIG. 28 is a section view through the brain stem depicted in FIG. 2A, showing the lateral hypothalamic area 112, as well as the paraventricular nucleus 100, dorsomedial nucleus 102, ventromedial nucleus 104, and arcuate nucleus 106.

The present invention provides electrical and/or drug stimulation to at least one or more of the above mentioned areas as a treatment for diabetes. Herein, stimulating drugs comprise medications, anesthetic agents, synthetic or natural hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an inhibitory drug is mentioned, this drug is acting in an inhibitory manner, although in other circumstances and/or locations, it may be an "excitatory" drug. In addition, stimulation of an area herein may include stimulation of cell bodies and axons in the area.

In some alternatives, an implantable signal generator and electrode(s) and/or an implantable pump and catheter(s) are used to deliver electrical stimulation and/or one or more stimulating drugs to specific areas in the brain. One or more electrodes are surgically implanted in the brain to provide electrical stimulation, and/or one or more catheters are implanted in the brain to infuse the stimulating drug(s).

In some embodiments, electrical stimulation is provided by one or more system control units (SCUs) that are small, implantable stimulators, referred to herein as microstimulators. The microstimulators of the present invention may be similar to or of the type referred to as BION® devices (see FIGS. 3A, 3B, and 3C). The following documents describe various details associated with the manufacture, operation and use of BION implantable microstimulators, and are all incorporated herein by reference:

| Application/Pat./ Publication No. | Filing/ Publication Date | Title |
|---|---|---|
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued June 28, 1994 | Implantable Microstimulator |
| U.S. Pat. No. 5,405,367 | Issued Apr. 11, 1995 | Structure and Method of Manufacture of an Implantable Microstimulator |
| PCT Publication WO 98/37926 | Published Sep. 3, 1998 | Battery-Powered Patient Implantable Device |
| PCT Publication WO 98/43700 | Published Oct. 8, 1998 | System of Implantable Devices For Monitoring and/or Affecting Body Parameters |
| PCT Publication WO 98/43701 | Published Oct. 8, 1998 | System of Implantable Devices For Monitoring and/or Affecting Body Parameters |
| U.S. Pat. No. 6,051,017 (App. No. 09/077,662) | Issued Apr. 18, 2000 (filed May 29, 1998) | Improved Implantable Microstimulator and Systems Employing Same |
| | Published September 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

Figure 3A:
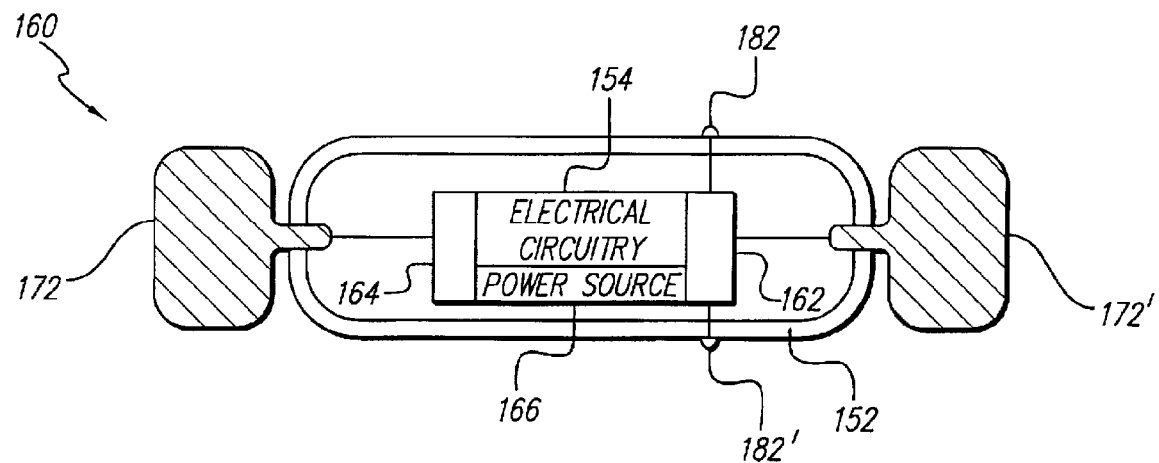
FIGS. 3A, 3B, and 3C show some possible configurations of an implantable microstimulator of the present invention.
Figure 3B:
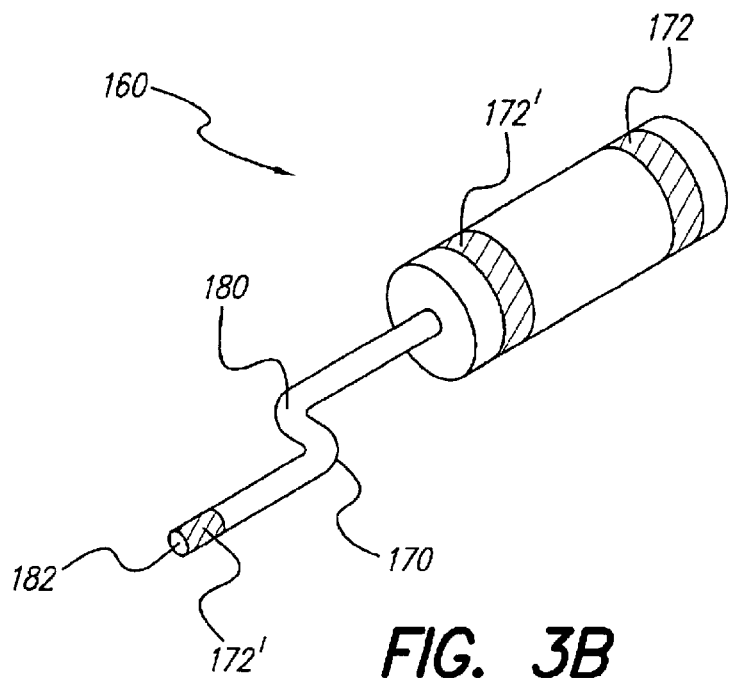
Figure 3C:
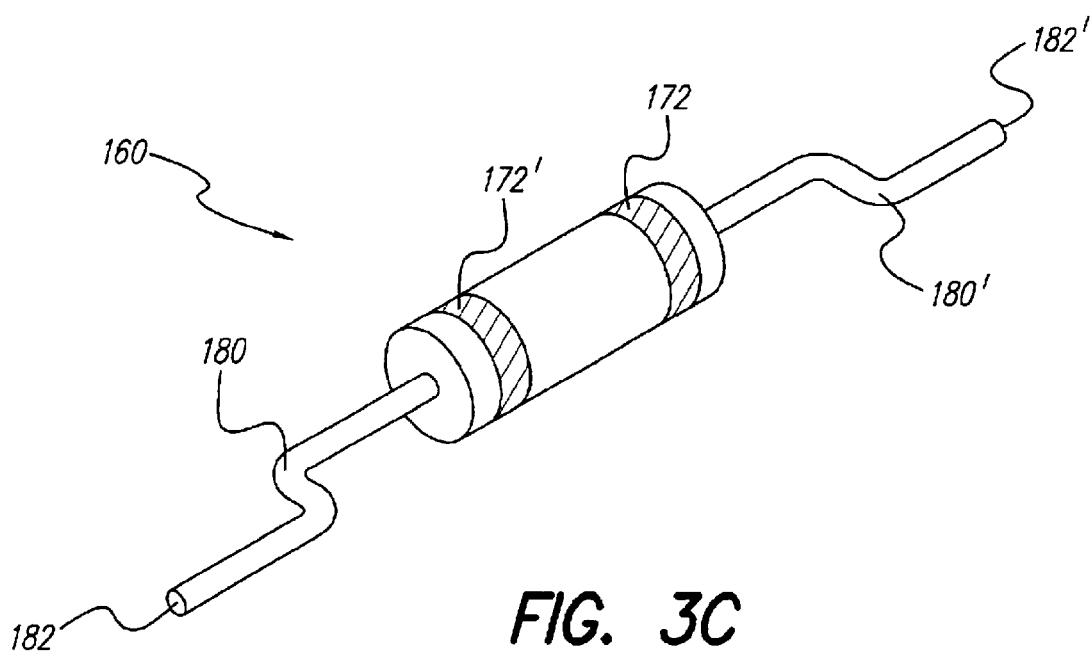

As shown in FIGS. 3A, 3B, and 3C, microstimulator SCUs 160 may include a narrow, elongated capsule 152 containing electronic circuitry 154 connected to electrodes 172 and 172', which may pass through the walls of the capsule at either end. Alternatively, electrodes 172 and/or 172' may be built into the case and/or arranged on a catheter 180 (FIG. 3B) or at the end of a lead, as described below. As detailed in the referenced patents, electrodes 172 and 172' generally comprise a stimulating electrode (to be placed close to the target tissue) and an indifferent electrode (for completing the circuit). Other configurations of microstimulator SCU 160 are possible, as is evident from the above-referenced patent publications, and as described in more detail herein.

Certain configurations of implantable microstimulator SCU 160 are sufficiently small to permit placement in or adjacent to the structures to be stimulated. For instance, in these configurations, capsule 152 may have a diameter of about 4–5 mm, or only about 3 mm, or even less than about 3 mm. In these configurations, capsule length may be about 25–35 mm, or only about 20–25 mm, or even less than about 20 mm. The shape of the microstimulator may be determined by the structure of the desired target, the surrounding area, and the method of implantation. A thin, elongated cylinder with electrodes at the ends, as shown in FIGS. 3A, 3B, and 3C, is one possible configuration, but other shapes, such as cylinders, disks, spheres, and helical structures, are possible, as are additional electrodes, infusion outlets, leads, and/or catheters.

Microstimulator SCU 160, when certain configurations are used, may be implanted with a surgical insertion tool such as the tool specially designed for the purpose, or may be injected (e.g., via a hypodermic needle). Alternatively, microstimulator SCU 160 may be implanted via conventional surgical methods, or may be inserted using other endoscopic or laparoscopic techniques. A more complicated surgical procedure may be required for fixing the microstimulator in place.

The external surfaces of microstimulator SCU 160 may advantageously be composed of biocompatible materials. Capsule 152 may be made of, for instance, glass or ceramic to provide a hermetic package that will exclude water vapor but permit passage of electromagnetic fields used to transmit data and/or power. Electrodes 172 and 172' may be made of a noble or refractory metal, such as platinum, iridium, tantalum, titanium, niobium or their alloys, in order to avoid corrosion or electrolysis which could damage the surrounding tissues and the device.

In certain embodiments of the instant invention, microstimulator SCU 160 comprises two, leadless electrodes. However, either or both electrodes 172 and 172' may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of microstimulator SCU 160, while allowing most elements of the microstimulator to be located in a more surgically convenient site. This minimizes the distance traversed and the surgical planes crossed by the device and any lead(s). In most uses of this invention, the leads are no longer than about 150 mm.

As mentioned earlier, stimulation is provided in accordance with the teachings of the present invention by electrical stimulation and/or one or more stimulating drugs. The invention includes one or more system control units (SCUs). In the case of electrical stimulation only, SCUs include a microstimulator and/or an implantable pulse/signal generator (IPG), or the like. In the case of drug infusion only, an SCU comprises an implantable pump or the like. In cases requiring both electrical stimulation and drug infusion, more than one SCU may be used. Alternatively, when needed and/or desired, an SCU provides both electrical stimulation and one or more stimulating drugs.

Figure 4:
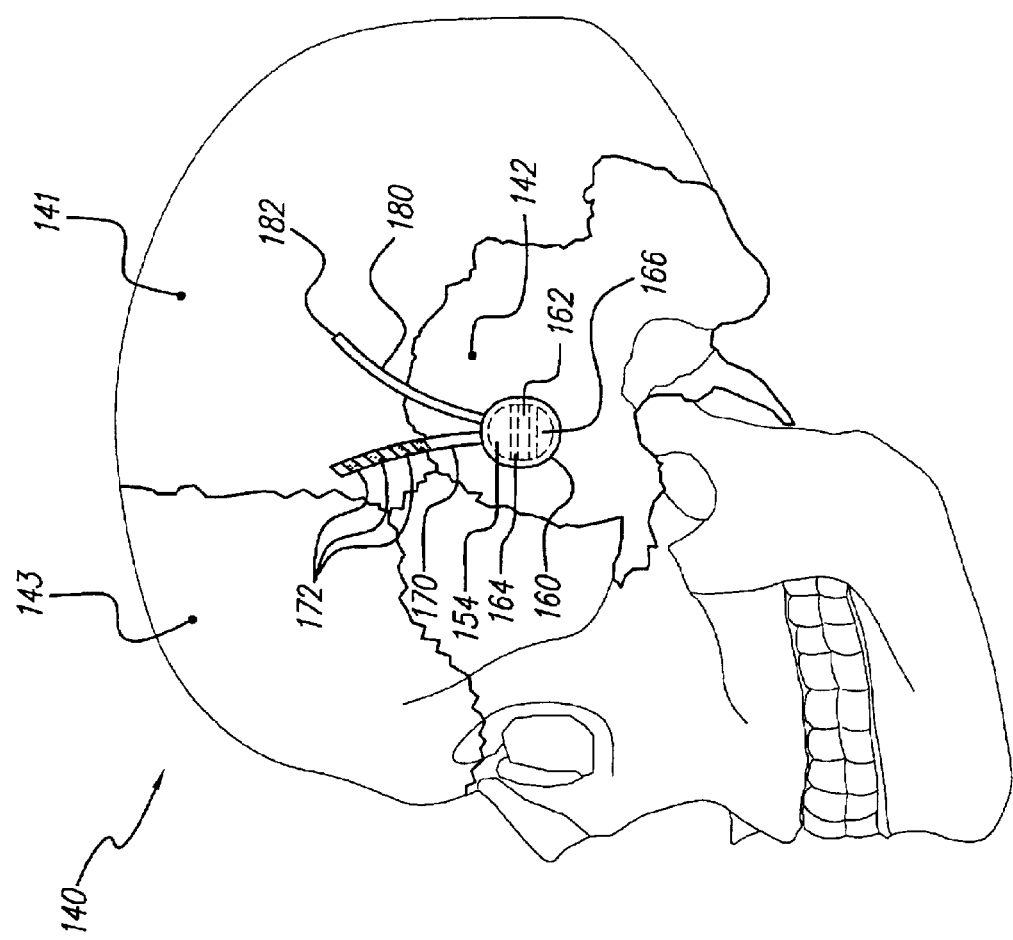
FIG. 4 illustrates a lateral view of the skull and components of some embodiments of the invention.

As depicted in FIG. 4, some embodiments of SCU 160 may be (but are not necessarily) implanted beneath the scalp, such as in a surgically-created shallow depression or opening in the skull 140, for instance, in parietal bone 141, temporal bone 142, or frontal bone 143. In several embodiments, SCU 160 conforms to the profile of surrounding tissue(s) and/or bone(s), and is small and compact. This may minimize upward pressure applied to the skin or scalp, which pressure may result in skin erosion or infection. In various embodiments, SCU 160 has a diameter of about 75 mm, or only about 65 mm, or even less than about 55 mm. In these configurations, SCU thickness may be approximately 10–12 mm, or even less than about 10 mm.

Figure 5:
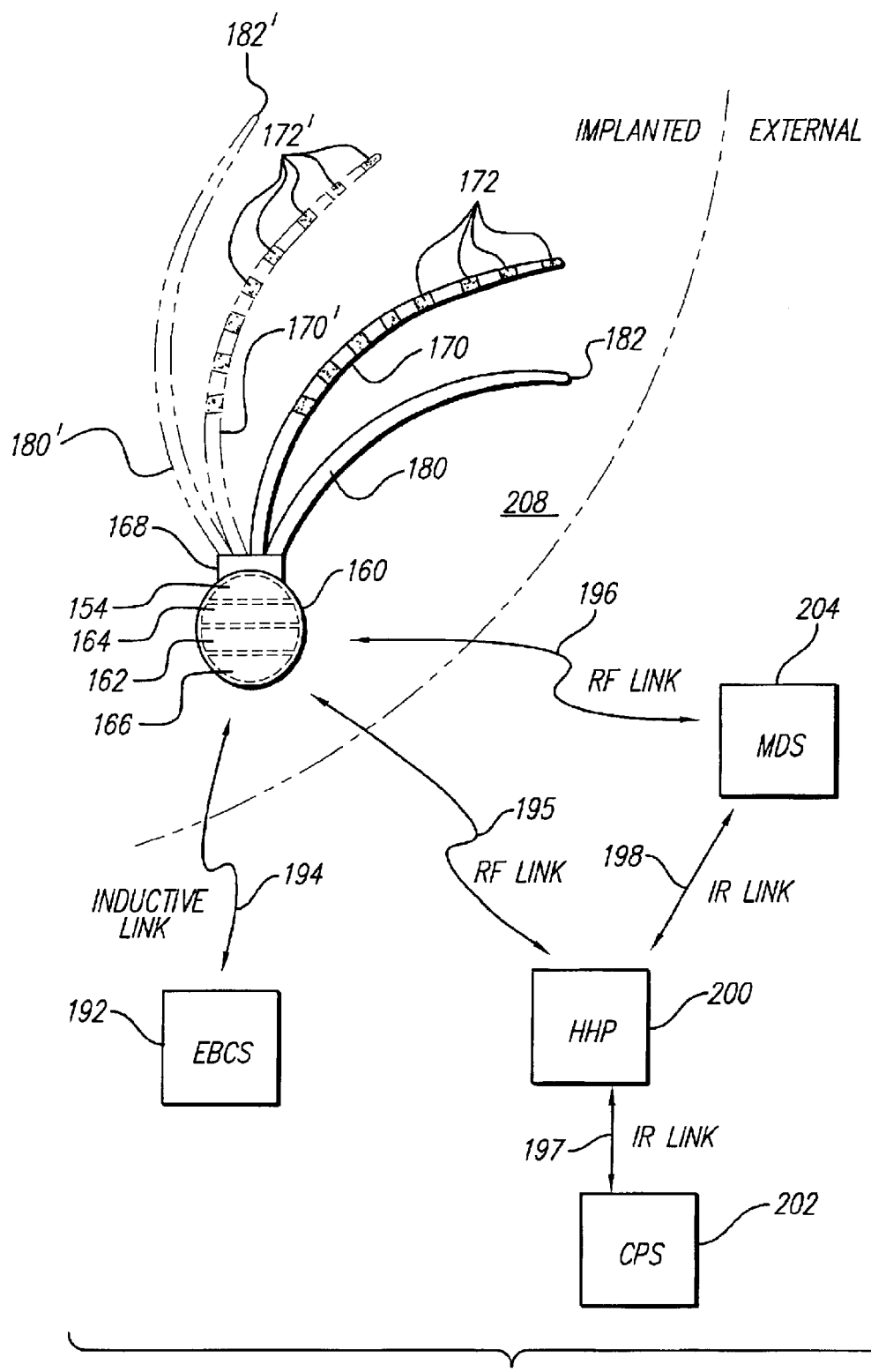
FIG. 5 illustrates internal and external components of certain embodiments of the invention.

As seen in the embodiments depicted in FIG. 5, one or more electrode leads 170 and/or catheters 180 attached to SCU 160 run subcutaneously, for instance, in a surgically-created shallow groove(s) in the skull, to an opening(s) in the skull, and pass through the opening(s) into or onto the brain parenchyma and surrounding tissue. Recessed placement of the SCU and the lead(s) and/or catheter(s) may decrease the likelihood of erosion of overlying skin, and may minimize any cosmetic impact.

In embodiments such as in FIG. 5, electrode(s) 172 are carried on lead 170 having a proximal end coupled to SCU 160. The lead contains wires electrically connecting electrodes 172 to SCU 160. SCU 160 contains electrical components 154 that produce electrical stimulation pulses that travel through the wires of lead 170 and are delivered to electrodes 172, and thus to the tissue surrounding electrodes 172. To protect the electrical components inside SCU 160, some or all of the case of the SCU may be hermetically sealed. For additional protection against, e.g., impact, the case may be made of metal (e.g. titanium) or ceramic, which materials are also, advantageously, biocompatible. In addition, SCU 160 may be configured to be Magnetic Resonance Imaging (MRI) compatible.

In some alternatives, the electrical stimulation may be provided as described in International Patent Application Serial Number PCT/US01/04417 (the '417 application), filed Feb. 12, 2001, which application is incorporated herein by reference in its entirety. As such, the electrical stimulation of the present invention may be as provided in this PCT application, which is directed to a "Deep Brain Stimulation System for the Treatment of Parkinson's Disease or Other Disorders".

In the case of treatment alternatively or additionally constituting drug infusion, SCU 160 may contain at least one pump 162 for storing and dispensing one or more drugs through infusion outlet(s) 182 and/or catheter(s) 180 into a predetermined site(s) in the brain tissue. When a catheter is used, it includes at least one infusion outlet 182, usually positioned at least at a distal end, while a proximal end of the catheter is connected to SCU 160.

According to some embodiments of the invention, such as described in the previously referenced '417 application and as depicted in FIG. 5, at least one lead 170 is attached to SCU 160, via a suitable connector 168, if necessary. Each lead includes at least two electrodes 172, and may include as many as sixteen or more electrodes 172. Additional leads 170' and/or catheter(s) 180' may be attached to SCU 160. Hence, FIG. 5 shows (in phantom lines) a second catheter 180', and a second lead 170', having electrodes 172' thereon, also attached to SCU 160. Similarly, the SCUs 160 of FIGS. 3A, 3B, and 3C have outlets 182, 182' for infusing a stimulating drug(s) and electrodes 172, 172' for applying electrical stimulation.

Lead(s) 170 of certain embodiments of the present invention may be less than about 5 mm in diameter, or even less than about 1.5 mm in diameter. Electrodes 172, 172' on leads 170, 170' may be arranged as an array, for instance, as two or more collinear electrodes, or even as four or more collinear electrodes, or they may not be collinear. A tip electrode may also be supplied at the distal end of one or more leads. In some embodiments, SCU 160 is programmable to produce either monopolar electrical stimulation, e.g., using the SCU case as an indifferent electrode, or bipolar electrical stimulation, e.g., using one of the electrodes of the electrode array as an indifferent electrode. Some embodiments of SCU 160 have at least four channels and drive up to sixteen electrodes or more.

SCU 160 (which herein refers to IPGs, implantable pumps, IPG/pump combinations, microstimulators for drug and/or electrical stimulation, other alternative devices described herein, and the like) contains, when necessary and/or desired, electronic circuitry 154 for receiving data and/or power from outside the body by inductive, radio frequency (RF), or other electromagnetic coupling. In some embodiments, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

SCU 160 also includes, when necessary and/or desired, a programmable memory 164 for storing a set(s) of data, stimulation, and control parameters. Among other things, memory 164 may allow electrical and/or drug stimulation to be adjusted to settings that are safe and efficacious with minimal discomfort for each individual. Specific parameters may provide therapy for various types and degrees of severity of diabetes. For instance, some patients may respond favorably to intermittent stimulation, while others may require continuous treatment for relief. In some embodiments, electrical and drug stimulation parameters are controlled independently. In various embodiments, they are coupled, e.g., electrical stimulation is programmed to occur only during drug infusion.

In addition, parameters may be chosen to target specific neural populations and to exclude others, or to increase neural activity in specific neural populations and to decrease neural activity in others. For example, relatively low frequency neurostimulation (i.e., less than about 100–150 Hz) typically has an excitatory effect on surrounding neural tissue, leading to increased neural activity, whereas relatively high frequency neurostimulation (i.e., greater than about 100–150 Hz) may have an inhibitory effect, leading to decreased neural activity. Similarly, excitatory neurotransmitters (e.g., acetylcholine), agonists thereof, and agents that increase levels of an excitatory neurotransmitter(s) (e.g., edrophonium) generally have an excitatory effect on neural tissue, while inhibitory neurotransmitters (e.g., gamma-aminobutyric acid, a.k.a. GABA), agonists thereof, and agents that act to increase levels of an inhibitory neurotransmitter(s) generally have an inhibitory effect. However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g. atropine) and agents that decrease levels of excitatory neurotransmitters may inhibit neural activity.

Some embodiments of SCU 160 also include a power source and/or power storage device 166. Possible power options for a stimulation device of the present invention, described in more detail below, include but are not limited to an external power source coupled to the stimulation device, e.g., via an RF link, a self-contained power source utilizing any means of generation or storage of energy (e.g., a primary battery, a rechargeable battery such as a lithium ion battery, an electrolytic capacitor, or a super- or ultra-capacitor), and if the self-contained power source is replenishable or rechargeable, means of replenishing or recharging the power source (e.g., an RF link).

In embodiments such as shown in FIG. 5, SCU 160 includes a rechargeable battery as a power source/storage device 166. The battery is recharged, as required, from an external battery charging system (EBCS) 192, typically through an inductive link 194. In these embodiments, and as explained more fully in the earlier referenced '417 PCT application, SCU 160 includes a processor and other electronic circuitry 154 that allow it to generate stimulation pulses that are applied to a patient 208 through electrodes 172 and/or outlet(s) 182 in accordance with a program and stimulation parameters stored in programmable memory 164. Stimulation pulses of drugs include various types and/or rates of infusion, such as intermittent infusion, infusion at a constant rate, and bolus infusion.

According to certain embodiments of the invention, an SCU operates independently. According to various embodiments of the invention, an SCU operates in a coordinated manner with other SCU(s), other implanted device(s), or other device(s) external to the patient's body. For instance, an SCU may control or operate under the control of another implanted SCU(s), other implanted device(s), or other device(s) external to the patient's body. An SCU may communicate with other implanted SCUs, other implanted devices, and/or devices external to a patient's body via, e.g., an RF link, an ultrasonic link, or an optical link. Specifically, an SCU may communicate with an external remote control (e.g., patient and/or physician programmer) that is capable of sending commands and/or data to an SCU and that may also be capable of receiving commands and/or data from an SCU.

For example, some embodiments of SCU 160 of the present invention may be activated and deactivated, programmed and tested through a hand held programmer (HHP) 200 (which may also be referred to as a patient programmer and may be, but is not necessarily, hand held), a clinician programming system (CPS) 202 (which may also be hand held), and/or a manufacturing and diagnostic system (MOS) 204 (which may also be hand held). HHP 200 may be coupled to SCU 160 via an RF link 195. Similarly, MDS 204 may be coupled to SCU 160 via another RF link 196. In a like manner, CPS 202 may be coupled to HHP 200 via an infra-red link 197; and MDS 204 may be coupled to HHP 200 via another infra-red link 198. Other types of telecommunicative links, other than RF or infra-red may also be used for this purpose. Through these links, CPS 202, for example, may be coupled through HHP 200 to SCU 160 for programming or diagnostic purposes. MDS 204 may also be coupled to SCU 160, either directly through the RF link 196, or indirectly through IR link 198, HHP 200, and RF link 195.

Figure 6:
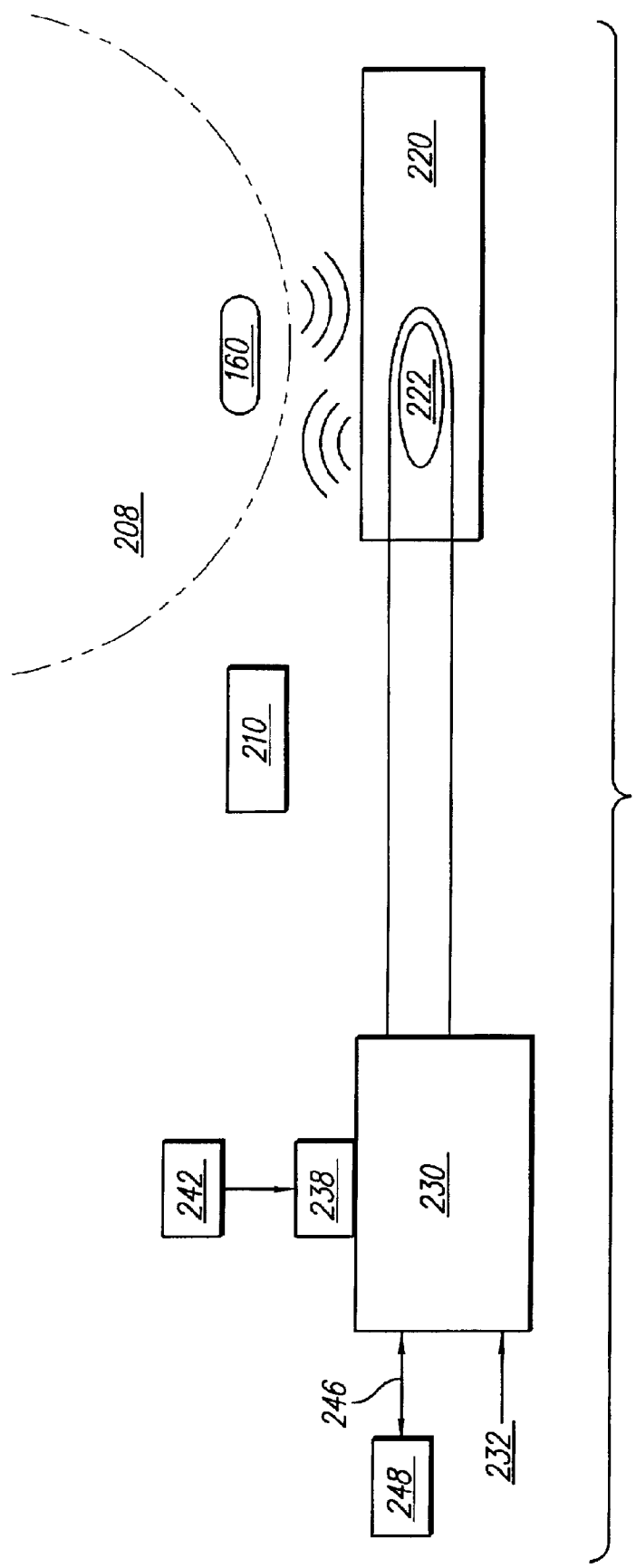
FIG. 6 illustrates external components of various embodiments of the invention.

In certain embodiments, using for example, a BION microstimulator(s) as described in the above referenced patents, and as illustrated in FIG. 6, the patient 208 switches SCU 160 on and off by use of controller 210, which may be handheld. Controller 210 operates to control SCU 160 by any of various means, including sensing the proximity of a permanent magnet located in controller 210, sensing RF transmissions from controller 210, or the like.

External components of various embodiments for programming and providing power to SCU 160 are also illustrated in FIG. 6. When it is required to communicate with SCU 160, patient 208 is positioned on or near external appliance 220, which appliance contains one or more inductive coils 222 or other means of communication (e.g., RF transmitter and receiver). External appliance 220 is connected to or is a part of external electronic circuitry appliance 230 which may receive power 232 from a conventional power source. External appliance 230 contains manual input means 238, e.g., a keypad, whereby the patient 208 or a caregiver 242 may request changes in electrical and/or drug stimulation parameters produced during the normal operation of SCU 160. In these embodiments, manual input means 238 includes various electromechanical switches and/or visual display devices that provide the patient and/or caregiver with information about the status and prior programming of SCU 160.

Alternatively or additionally, external electronic appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

The external appliance(s) may be embedded in a cushion, pillow, or hat. Other possibilities exist, including a head band or other structure that may be affixed to the patient's body or clothing.

In order to help determine the strength and/or duration of electrical stimulation and/or the amount and/or type(s) of stimulating drug(s) required to produce the desired effect, in some embodiments, a patient's response to and/or need for treatment is sensed. For example, electrical activity of the brain (e.g., EEG), nerve activity (e.g., ENG), muscle activity (e.g., EMG), or other activity may be sensed. Additionally or alternatively, one or more neurotransmitter levels and/or their associated breakdown product levels, hormone levels, levels of one or more catecholamines, or other substances, such as ketone levels, glucose levels, electrolyte, enzyme, cytokine, medication and/or other drug levels and/or changes in these or other substances in the blood plasma or local interstitial fluid, may be sensed. For example, levels of one or more neurotransmitters, such as Neuropeptide Y (NPY) and/or serotonin, may be sensed. Levels of one or more hormones or other substances, such as adrenocorticotrophic hormone (ACTH), luteinizing hormone (LH), follicle-stimulating hormone (FSH), growth hormone (GH), thyroid stimulating hormone (TSH), leptin, ghrelin, agouti-related protein (AGRP), orexin-A, orexin-B, cholecystokinin (CCK), glucagon, glucocorticoids, and the like may be sensed.

For example, when electrodes of SCU 160 are implanted adjacent to the arcuate nucleus 106 of the hypothalamus, a stimulating electrode of SCU 160, or other sensing means, may be used to sense changes in NPY level resulting from the electrical and/or drug stimulation applied to the arcuate nucleus 106. (As used herein, "adjacent" or "unear" means as close as reasonably possible to targeted tissue, including touching or even being positioned within the tissue, but in general, may be as far as about 150 mm from the target tissue.)

Alternatively, an "SCU" dedicated to sensory processes communicates with an SCU that provides the stimulation pulses. The implant circuitry 154 may, if necessary, amplify and transmit these sensed signals, which may be digital or analog. Other methods of determining the required electrical and/or drug stimulation include measuring impedance, acidity/alkalinity (via a pH sensor), body mass, and other methods mentioned herein, and others that will be evident to those of skill in the art upon review of the present disclosure. The sensed information may be used to control stimulation parameters in a closed-loop manner.

For instance, in several embodiments of the present invention, a first and second "SCU" are provided. The second "SCU" periodically (e.g. once per minute) records NPY level (or the level of some other substance, or an amount of electrical activity, etc.), which it transmits to the first SCU. The first SCU uses the sensed information to adjust electrical and/or drug stimulation parameters according to an algorithm programmed, e.g., by a physician. For example, the amplitude of electrical stimulation may be increased in response to increased NPY levels. In some alternatives, one SCU performs both the sensing and stimulating functions, as discussed in more detail presently.

While an SCU 160 may also incorporate means of sensing diabetes or symptoms or other prognostic or diagnostic indicators of diabetes, e.g., via levels of a neurotransmitter or hormone, it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted SCU(s) 160. However, in some cases, it may not be necessary or desired to include a sensing function or device, in which case stimulation parameters are determined and refined, for instance, by patient feedback, or the like.

Thus, it is seen that in accordance with the present invention, one or more external appliances may be provided to interact with SCU 160, and may be used to accomplish, potentially among other things, one or more of the following functions:

Function 1: If necessary, transmit electrical power from the external electronic appliance 230 via appliance 220 to SCU 160 in order to power the device and/or recharge the power source/storage device 166. External electronic appliance 230 may include an automatic algorithm that adjusts electrical and/or drug stimulation parameters automatically whenever the SCU(s) 160 is/are recharged.

Function 2: Transmit data from the external appliance 230 via the external appliance 220 to SCU 160 in order to change the parameters of electrical and/or drug stimulation produced by SCU 160.

Function 3: Transmit sensed data indicating a need for treatment or in response to stimulation from SCU 160 (e.g., electrical activity of the brain, nerve activity, muscle activity, neurotransmitter levels, levels of neurotransmitter breakdown products, impedance, acidity/alkalinity, medication levels, hormone levels, or other activity) to external appliance 230 via external appliance 220.

Function 4: Transmit data indicating state of the SCU 160 (e.g., battery level, drug level, stimulation parameters, etc.) to external appliance 230 via external appliance 220.

By way of example, a treatment modality for diabetes may be carried out according to the following sequence of procedures:

1. An SCU 160 is implanted so that its electrodes 172 and/or infusion outlet 182 are located in or near the arcuate nucleus 106 of the hypothalamus. If necessary or desired, electrodes 172' and/or infusion outlet(s) 182' may additionally or alternatively be located in or adjacent to the paraventricular nucleus 100, dorsomedial nucleus 102, and/or any other neural tissue with receptors for NPY.

2. Using Function 2 described above (i.e., transmitting data) of external electronic appliance 230 and external appliance 220, SCU 160 is commanded to produce a series of electrical stimulation pulses, possibly with gradually increasing amplitude, and possibly while infusing gradually increasing amounts of an excitatory neurotransmitter antagonist, e.g., a muscarinic antagonist, such as atropine, benztropine, or scopolamine.

3. After each stimulation pulse, or at some other predefined interval, any change in NPY level resulting from the electrical and/or drug stimulation is sensed, for instance, by one or more electrodes 172 and/or 172'. These responses are converted to data and telemetered out to external electronic appliance 230 via Function 3.

4. From the response data received at external appliance 230 from SCU 160, the stimulus threshold for obtaining a response is determined and is used by a clinician 242 acting directly 238 or by other computing means 248 to transmit the desired electrical and/or drug stimulation parameters to SCU 160 in accordance with Function 2.

5. When patient 208 desires to invoke electrical stimulation and/or drug infusion, patient 208 employs controller 210 to set SCU 160 in a state where it delivers a prescribed stimulation pattern from a predetermined range of allowable stimulation patterns.

6. To cease electrical and/or drug stimulation, patient 208 employs controller 210 to turn off SCU 160.

7. Periodically, the patent or caregiver recharges the power source/storage device 166 of SCU 160, if necessary, in accordance with Function 1 described above (i.e., transmit electrical power).

For the treatment of any of the various types and degrees of severity of diabetes, it may be desirable to modify or adjust the algorithmic functions performed by the implanted and/or external components, as well as the surgical approaches, in ways that would be obvious to skilled practitioners of these arts. For example, in some situations, it may be desirable to employ more than one SCU 160, each of which could be separately controlled by means of a digital address. Multiple channels and/or multiple patterns of electrical and/or drug stimulation might thereby be programmed by the clinician and controlled by the patient in order to deal with complex or multiple diseases, symptoms, or dysfunctions.

In some embodiments discussed earlier, SCU 160, or a group of two or more SCUs, is controlled via closed-loop operation. A need for and/or response to stimulation is sensed via SCU 160, or by an additional SCU (which may or may not be dedicated to the sensing function), or by another implanted or external device. Sensed conditions may be one or more of body mass, impedance, acidity/alkalinity (via a pH sensor), electrical activity of the brain (e.g., EEG), nerve activity (e.g., ENG), muscle activity (e.g., EMG), or other activity. Additionally or alternatively, neurotransmitter levels and/or their associated breakdown product levels, hormone levels, or other substances, such as ketone levels, cytokines, glucose, electrolytes, enzymes, medication, and/or other drug levels, levels of one or more catecholamines, and/or any other bloodborne substance may be sensed. For example, levels of one or more neurotransmitters, such as Neuropeptide Y (NPY) and/or serotonin, may be sensed. Levels of one or more hormones or other substances, such as adrenocorticotrophic hormone (ACTH), luteinizing hormone (LH), follicle-stimulating hormone (FSH), growth hormone (GH), thyroid stimulating hormone (TSH), leptin, ghrelin, agouti-related protein (AGRP), orexin-A, orexin-B, cholecystokinin (CCK), glucagon, glucocorticoids, and the like may be sensed.

If necessary, the sensed information is transmitted to SCU 160. In some embodiments, the parameters used by SCU 160 are automatically adjusted based on the sensed information. Thus, the electrical and/or drug stimulation parameters are adjusted in a closed-loop manner to provide stimulation tailored to the need for and/or response to the electrical and/or drug stimulation.

Figure 7:
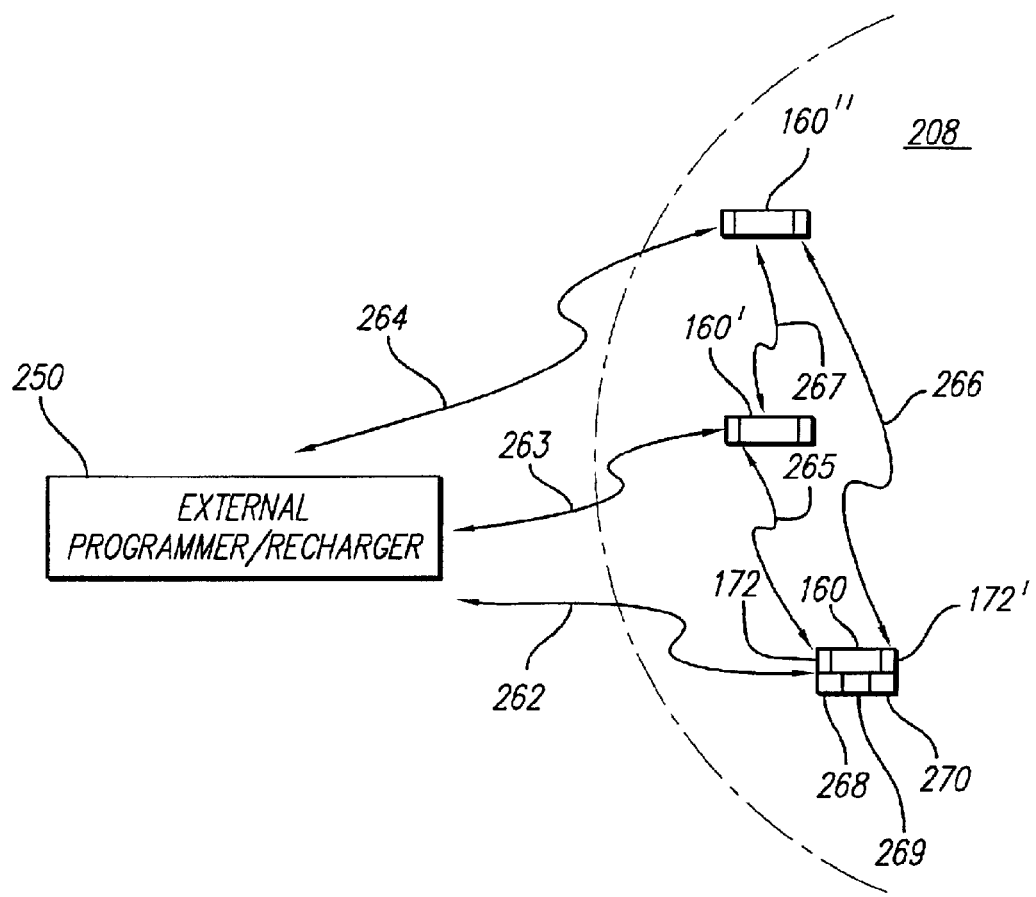
FIG. 7 depicts a system of implantable devices that communicate with each other and/or with external control/programming devices.

For instance, as shown in the example of FIG. 7, a first SCU 160, implanted beneath the skin of the patient 208, provides a first medication or substance; a second SCU 160' provides a second medication or substance; and a third SCU 160' provides electrical stimulation via electrodes 172 and 172'. As mentioned earlier, the implanted devices may operate independently or may operate in a coordinated manner with other similar implanted devices, other implanted devices, or other devices external to the patient's body, as shown by the control lines 262, 263 and 264 in FIG. 7. That is, in accordance with certain embodiments of the invention, the external controller 250 controls the operation of each of the implanted devices 160, 160' and 160". According to various embodiments of the invention, an implanted device, e.g. SCU 160, may control or operate under the control of another implanted device(s), e.g. SCU 160' and/or SCU 160". That is, a device made in accordance with the invention may communicate with other implanted stimulators, other implanted devices, and/or devices external to a patient's body, e.g., via an RF link, an ultrasonic link, an optical link, or the like. Specifically, as illustrated in FIG. 7, SCU 160, 160', and/or 160", made in accordance with the invention, may communicate with an external remote control (e.g., patient and/or physician programmer 250) that is capable of sending commands and/or data to implanted devices and that may also be capable of receiving commands and/or data from implanted devices.

A drug infusion stimulator made in accordance with the invention may incorporate communication means for communicating with one or more external or site specific drug delivery devices, and, further, may have the control flexibility to synchronize and control the duration of drug delivery. The associated drug delivery device typically provides a feedback signal that lets the control device know it has received and understood commands. The communication signal between the implanted stimulator and the drug delivery device may be encoded to prevent the accidental or inadvertent delivery of drugs by other signals.

An SCU made in accordance with the invention thus incorporates, in some embodiments, first sensing means 268 for sensing therapeutic effects, clinical variables, or other indicators of the state of the patient, such as EEG, ENG, EMG, impedance, pH, body mass, or the like. The stimulator additionally or alternatively incorporates second means 269 for sensing neurotransmitter levels and/or their associated breakdown product levels, medication levels and/or other drug levels, hormone, glucose, ketone, electrolytes, enzyme, and/or cytokine levels and/or changes in these or other substances in the blood plasma or local interstitial fluid. The stimulator additionally or alternatively incorporates third means 270 for sensing electrical current levels and/or waveforms supplied by another source of electrical energy.

Sensed information may be used to control infusion and/or electrical parameters in a closed loop manner, as shown by control lines 266, 267, and 265. Thus, the sensing means may be incorporated into a device that also includes electrical and/or drug stimulation, or the sensing means (that may or may not have stimulating means) may communicate the sensed information to another device(s) with stimulating means.

According to certain embodiments of the invention, the electrical and/or drug stimulation increases excitement of one or more of those areas of the brain that exhibit chronic decreased activity in diabetic patients relative to control subjects, thereby treating or preventing diabetes and the symptoms and pathological consequences thereof. This decreased activity could be due to decreased levels or activity of an excitatory neurotransmitter and/or increased levels or activity of an inhibitory neurotransmitter, and may be present in other metabolic disorders, such as obesity and other eating disorders. Such excitatory stimulation is likely to be produced by low-frequency electrical stimulation (e.g., less than about 100–150 Hz), an excitatory neurotransmitter agonist(s) (e.g., acetylcholine), a medication that increases the level of an excitatory neurotransmitter (e.g., edrophonium), an excitatory hormone agonists(s), an inhibitory neurotransmitter antagonist(s) (e.g., bicuculline), an inhibitory hormone antagonist(s), corticotropin releasing factor (CRF) and/or its agonists, bombesin and/or its agonists, glucagon-like peptide 1 and/or its agonists, serotonin and/or its agonists, leptin and/or its agonists, ghrelin antagonists, AGRP antagonists, MC4-R agonists, MC3-R agonists, orexin-A antagonists, orexin-B antagonists, OX1R antagonists, OX2R antagonists, cholecystokinin and/or its agonists, and/or the like. For example, this excitatory stimulation may be applied to, among other places, one or more of the paraventricular nucleus 100, the ventromedial nucleus 104, the dorsal motor nucleus of the vagus nerve 108, and the nucleus of the solitary tract 110.

According to other embodiments of the invention, the electrical and/or drug stimulation decreases excitement of one or more of those areas of the brain that exhibit chronic increased activity in diabetic patients relative to control subjects, thereby treating or preventing diabetes. This increased activity could be due to increased levels or activity of an excitatory neurotransmitter and/or decreased levels or activity of an inhibitory neurotransmitter, and may be present in other metabolic disorders, such as obesity and other eating disorders. Such inhibitory stimulation is likely to be produced by high-frequency electrical stimulation (e.g., greater than about 100–150 Hz), an inhibitory neurotransmitter agonist(s) (e.g., GABA), a medication that increases the level of an inhibitory neurotransmitter, an inhibitory hormone agonist(s), an excitatory neurotransmitter antagonist(s) (e.g., atropine), an excitatory hormone antagonist(s), and/or the like. As another example, inhibitory stimulation may also/instead be applied to, among other places, one or both of the arcuate nucleus 106 and the lateral hypothalamic area 112.

According to some embodiments of the invention, the stimulation inhibits the secretion of NPY by the NPY-secreting cells of the arcuate nucleus 106 of the hypothalamus. Such inhibitory action is likely to be produced by high-frequency electrical stimulation, an inhibitory neurotransmitter agonist(s), an inhibitory hormone agonist(s), an excitatory neurotransmitter antagonist(s), an excitatory hormone antagonist(s), insulin, leptin, serotonin, corticotropin releasing factor (CRF), and/or the like.

According to various embodiments of the invention, the stimulation inhibits the effects of NPY on the paraventricular nucleus 100, the dorsomedial nucleus 102, the ventromedial nucleus 104, and/or any other neural tissue with receptors for NPY. Such inhibitory action is likely to be produced by high-frequency electrical stimulation, an antagonist(s) of NPY (e.g., PYX-1, BIBP 3226, 1229 U91, and/or NGD 95-1), and/or the like applied to one or more of the paraventricular nucleus 100, the dorsomedial nucleus 102, the ventromedial nucleus 104, and the arcuate nucleus 106.

According to various embodiments of the invention, the stimulation inhibits the production of AGRP by the AGRP-producing cells of the arcuate nucleus 106. This inhibitory action is likely to be produced by high-frequency electrical stimulation, an inhibitory neurotransmitter agonist(s), a medication that increases the level of an inhibitory neurotransmitter, an inhibitory hormone agonist(s), an excitatory neurotransmitter antagonist(s), an excitatory hormone antagonist(s), insulin, and/or the like.

According to certain embodiments of the invention, the stimulation inhibits the effects of AGRP on the paraventricular nucleus 100, the dorsomedial nucleus 102, the arcuate nucleus 106, and/or any other neural tissue with receptors for AGRP. Such inhibitory stimulation is likely to be produced by high-frequency electrical stimulation, an inhibitory neurotransmitter agonist(s), a medication that increases the level of an inhibitory neurotransmitter, an inhibitory hormone agonist(s), an excitatory neurotransmitter antagonist(s), an excitatory hormone antagonist(s), and/or the like.

According to some embodiments of the invention, the stimulation acts as an agonist of MC4-R and/or MC3-R in the paraventricular nucleus 100, dorsomedial nucleus 102, and/or arcuate nucleus 106. Such excitatory stimulation is likely to be produced by low-frequency electrical stimulation, an excitatory neurotransmitter agonist(s), an excitatory hormone agonist(s), an inhibitory neurotransmitter antagonist(s), an inhibitory hormone antagonist(s), and/or the like.

According to various embodiments of the invention, the stimulation inhibits the production of orexins by the lateral hypothalamus 112, and/or inhibits the action of orexins, for instance by acting as an antagonist(s) of the orexin-A receptor (OX1R) and/or orexin-B receptor (OX2R), in the paraventricular nucleus 100 and/or ventromedial nucleus 104. Such inhibitory stimulation is likely to be produced by high-frequency electrical stimulation, an inhibitory neurotransmitter agonist(s), an inhibitory hormone agonist(s), an excitatory neurotransmitter antagonist(s), an excitatory hormone antagonist(s), and/or the like.

According to some embodiments of the invention, the stimulation inhibits the effects of one or more catecholamines on the paraventricular nucleus 100, the dorsomedial nucleus 102, and/or any other neural tissue with receptors for catecholamines. Such inhibitory action is likely to be produced by high-frequency electrical stimulation, an antagonist(s) of the catecholamine(s) (e.g., prazosin, metoprolol, and/or carvedilol), and/or the like applied to at least one of the paraventricular nucleus 100 and the dorsomedial nucleus 102.

According to certain embodiments of the invention, the stimulation increases secretion of corticotropin-releasing factor (CRF) by the arcuate nucleus 106 of the hypothalamus. Such excitatory stimulation is likely to be produced by low-frequency electrical stimulation, an excitatory neurotransmitter agonist(s), an excitatory hormone agonist(s), an inhibitory neurotransmitter antagonist(s), an inhibitory hormone antagonist(s), and/or the like.

According to some embodiments of the invention, the stimulation increases secretion of gonadotropin-releasing hormone (GnRH), luteinizing hormone releasing hormone (LHRH), and/or thyrotropin releasing hormone (TRH) by the arcuate nucleus 106 of the hypothalamus. Such excitatory stimulation is likely to be produced by low-frequency electrical stimulation, an excitatory neurotransmitter agonist (s), an excitatory hormone agonist(s), an inhibitory neurotransmitter antagonist(s), an inhibitory hormone antagonist(s), and/or the like.

According to several embodiments of the invention, the stimulation inhibits the effects of gamma-aminobutyric acid (GABA) on the ventromedial nucleus 104 of the hypothalamus and/or any other neural tissue with receptors for GABA. Such inhibitory action is likely to be produced by high-frequency electrical stimulation, an antagonist(s) of GABA (e.g., bicuculline), and/or the like.

In certain embodiments, sensing means described earlier may be used to orchestrate first the activation of SCU(s) targeting one or more areas of the brain, and then, when appropriate, the SCU(s) targeting another area(s) and/or by a different means. Alternatively, this orchestration may be programmed, and not based on a sensed condition.

Additional potential (but not necessary) uses of the present invention include, but are not limited to, application to diabetes prevention (via the promotion of normal metabolism and weight reduction), obesity and other eating disorders, and other metabolic disorders.

While the invention herein disclosed has been described by means of specific embodiments and applications thereof, numerous modifications and variations could be made thereto by those skilled in the art without departing from the scope of the invention set forth in the claims.

What is claimed is:

1. A method of preventing diabetes or treating patients with diabetes, comprising:
   implanting at least one system control unit in at least one of the skull and the brain of the patient, wherein the at least one unit controls the delivery of at least one stimulus to at least one area of the brain affecting diabetes;
   applying the at least one stimulus to the at least one area of the brain that exhibits chronic abnormal activity, in order to prevent or treat diabetes,
   wherein the area is the nucleus of the solitary tract.

2. The method of claim 1 wherein the at least one system control unit is connected to at least two electrodes, and wherein the stimulus composes electrical simulation delivered via the at least two electrodes.

3. The method of claim 1 wherein the at least one system control unit is connected to at least one pump and at least one infusion outlet, and wherein the stimulus comprises stimulation via one or more drugs delivered from the at least one pump through the at least one outlet.

4. The method of claim 1 wherein the stimulus is at least one stimulating drug.

5. The method of claim 1 wherein the stimulus is electrical stimulation.

6. The method of claim 1 wherein the stimulus is electrical stimulation and at least one stimulating drug.

7. The method of claim 1 further comprising applying the stimulus in coordination with delivery of a medication.

8. The method of claim 1 further comprising sensing at least one condition and using the at least one sensed condition to automatically determine the stimulus to apply.

9. The method of claim 1 further comprising implanting more than one system control unit.

10. The method of claim 1 wherein implanting at least one system control unit comprises implanting at least one microstimulator.

11. A method of preventing metabolic disorders or treating patients with metabolic disorders, comprising:
    implanting at least one system control unit in at least one of the skull and the brain of the patient, wherein the at least one unit controls the delivery of at least one stimulus to at least one area of the brain affecting a metabolic disorder;
    applying the at least one stimulus to the at least one area of the brain that exhibits chronic abnormal activity, in order to prevent or treat the metabolic disorder,
    wherein the area is the nucleus of the solitary tract.

12. The method of claim 11, further comprising:
    sensing at least one condition indicating a need for said at least one stimulus in order to treat or prevent metabolic disorder;
    wherein the at least one sensed condition is at least one of electrical activity of the brain, nerve activity, muscle activity, body mass, impedance, pH, neurotransmitter level, neurotransmitter breakdown product level, hormone level, ketone level, glucose level, electrolyte level, enzyme level, cytokine level, medication level, other drug level, and level of any other bloodborne substance.

13. The method of claim 12 wherein the at least one system control unit is configured to use the sensed condition to control the delivery of the at least one stimulus.

14. The method of claim 12 wherein the at least one sensed condition is the level of one or more of Neuropeptide Y (NPY), serotonin, one or more catecholamines, adrenocorticotrophic hormone (ACTH), luteinizing hormone (LH), follicle-stimulating hormone (FSH), growth hormone (GH), thyroid stimulating hormone (TSH), leptin, ghrelin, AGRP, orexin-A, orexin-B, cholecystokinin (CCK), glucagon, and glucocorticoids.

15. The method of claim 11 wherein implanting the at least one system control unit further comprises:
    implanting at least one pump, the pump having:
        at least one infusion outlet; and
        fluid connections connecting the at least one pump to the at least one infusion outlet; and
    wherein the at least one stimulus is at least one stimulating drug delivered to the at least one area of the brain in order to treat or prevent metabolic disorders.

16. The method of claim 15 wherein the at least one pump and the at least one infusion outlet are further configured to deliver a liquid that increases excitement of the at least one area of the brain that exhibits chronic decreased activity; and
    wherein the at least one area of the brain the nucleus of the solitary tract.

17. The method of claim 16 wherein the at least one pump and the at least one infusion outlet are further configured to deliver at least one of an excitatory neurotransmitter agonist, a medication that increases levels of at least one excitatory neurotransmitter, an excitatory hormone agonist, an inhibitory neurotransmitter antagonist, an inhibitory hormone antagonist, corticotropin releasing factor, a corticotropin releasing factor agonist, bombesin, a bombesin agonist, glucagon-like peptide 1, a glucagon-like peptide 1 agonist, serotonin, a serotonin agonist, leptin, a leptin agonist, a ghrelin antagonist, an AGRP antagonist, an MC4-R agonist, an MC3-R agonist, an orexin-A antagonist, an orexin-B antagonist, an OX1R antagonist an OX2R antagonist cholecystokinin, end a cholecystokinin agonist.

18. The method of claim 15 wherein the at least one pump and the at least one infusion outlet are further configured to deliver a liquid that decreases excitement of the at least one area of the brain that exhibits chronic increased activity.

19. The method of claim 18 wherein the at least one pump and the at least one infusion outlet are further configured to deliver at least one of an inhibitory neurotransmitter agonist, a medication that increases the level of an inhibitory neurotransmitter, an inhibitory hormone agonist, an excitatory neurotransmitter antagonist, and/or an excitatory hormone antagonist.

20. The method of claim 11 wherein implanting the at least one system control unit further comprises:
   implanting at least two electrodes configured to apply electrical stimulation to the at least one area of the brain in order to prevent or treat metabolic disorders; and
   connecting the at least one system control unit to the at least two electrodes, through which the electrical stimulation is delivered to the at least one area adjacent to the electrodes.

21. The method of claim 20 wherein the at least one system control unit is further configured to control the delivery of electrical stimulation pulses at less than about 100 to 150 Hz; and
   wherein the at least one area of the brain is the nucleus of the solitary tract.

22. The method of claim 20 wherein the at least one system control unit is further configured to control the delivery of electrical simulation pulses at greater than about 100 to 150 Hz.

23. The method of claim 11 wherein the at least one system control unit is configured to conform to the profile of the skull.

24. The method of claim 11 wherein the at least one system control unit is at least one microstimulator.

* * * * *